(12) United States Patent
Fukumoto et al.

(10) Patent No.: US 9,179,889 B2
(45) Date of Patent: Nov. 10, 2015

(54) ULTRASONIC DIAGNOSTIC DEVICE, AND METHOD FOR MEASURING INITMA-MEDIA COMPLEX THICKNESS

(75) Inventors: Takenori Fukumoto, Kanagawa (JP); Akihiro Kawabata, Kanagawa (JP); Makiko Urabe, Tokyo (JP); Takao Suzuki, Kanagawa (JP); Yushi Nishimura, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 435 days.

(21) Appl. No.: 13/496,832

(22) PCT Filed: Nov. 12, 2010

(86) PCT No.: PCT/JP2010/006661
§ 371 (c)(1),
(2), (4) Date: Mar. 16, 2012

(87) PCT Pub. No.: WO2011/099103
PCT Pub. Date: Aug. 18, 2011

(65) Prior Publication Data
US 2012/0179042 A1  Jul. 12, 2012

(30) Foreign Application Priority Data
Feb. 10, 2010 (JP) .................................. 2010-027246

(51) Int. Cl.
*A61B 8/02* (2006.01)
*A61B 8/08* (2006.01)

(52) U.S. Cl.
CPC ............. *A61B 8/0858* (2013.01); *A61B 8/0891* (2013.01); *A61B 8/5284* (2013.01)

(58) Field of Classification Search
CPC ... A61B 8/0858; A61B 8/0891; A61B 8/5284
USPC .................................. 600/437, 443, 459, 467
See application file for complete search history.

(56) References Cited

U.S. PATENT DOCUMENTS 6,132,373 A * 10/2000 Ito et al. .......................... 600/437
7,338,452 B2 * 3/2008 Shiina et al. .................... 600/467
8,079,958 B2 * 12/2011 Satoh et al. ..................... 600/443
8,465,426 B2 * 6/2013 Kanai et al. ..................... 600/437
2007/0055149 A1  3/2007 Suzuki et al.

(Continued)

FOREIGN PATENT DOCUMENTS

JP  2000-229082  8/2000
JP  2008/168016 A  7/2008

(Continued)

OTHER PUBLICATIONS

Chinese Office Action, Notification of First Office Action, Application No. 201080036008.3, Mailing Date: Feb. 28, 2014 (12 pages).

(Continued)

*Primary Examiner* — Baisakhi Roy
(74) *Attorney, Agent, or Firm* — Lucas & Mercanti, LLP

(57) ABSTRACT

An ultrasonic diagnostic apparatus according to the present invention includes: an ultrasonic signal processing section, which performs transmission processing for transmitting an ultrasonic wave toward a subject's blood vessel by driving a probe and reception processing for generating a received signal based on the ultrasonic wave reflected from the subject's blood vessel and received at the probe; a tomographic image processing section, which generates a tomographic image based on the received signal; a boundary detecting section, which detects the lumen-intima and media-adventitia boundaries of the blood vessel based on the received signal or the tomographic image; a vascular wall thickness calculating section, which calculates, as a vascular wall thickness value, the interval between the lumen-intima and media-adventitia boundaries detected by the boundary detecting section; a reliability determining section, which determines the reliability of the vascular wall thickness value by a signal feature of the received signal or an image information feature of the tomographic image at a location on the lumen-intima and/or media-adventitia boundaries detected; and a control section, which decides, in accordance with the decision made by the reliability determining section, that the vascular wall thickness value be defined as an intima-media thickness.

26 Claims, 16 Drawing Sheets

(56) References Cited

U.S. PATENT DOCUMENTS

| | | |
|---|---|---|
| 2008/0051658 A1* | 2/2008 | Demi et al. .................. 600/441 |
| 2008/0125651 A1 | 5/2008 | Watanabe et al. |
| 2008/0171939 A1 | 7/2008 | Ishihara |
| 2009/0030324 A1* | 1/2009 | Kato et al. .................. 600/459 |
| 2010/0016721 A1* | 1/2010 | Kanai et al. .................. 600/443 |
| 2010/0063391 A1 | 3/2010 | Kanai |
| 2010/0113930 A1* | 5/2010 | Miyachi .................. 600/443 |
| 2010/0210946 A1* | 8/2010 | Harada et al. .................. 600/443 |
| 2011/0096958 A1 | 4/2011 | Fukumoto |

FOREIGN PATENT DOCUMENTS

| | | |
|---|---|---|
| JP | 2009-039277 A | 2/2009 |
| JP | 2009-153573 A | 7/2009 |
| JP | 2010-022565 | 2/2010 |
| WO | 2004/103185 A1 | 12/2004 |
| WO | 2005/002446 A1 | 1/2005 |
| WO | 2008/023618 A | 2/2008 |
| WO | 2010/001564 A1 | 1/2010 |

OTHER PUBLICATIONS

English translation of Chinese Office Action, Notification of First Office Action, Application No. 201080036008.3, Mailing Date: Feb. 28, 2014 (27 pages).

Japanese Office Action, Notice of Reasons for Rejection, Japanese Application No. 2011-553665. Dispatch Date: Apr. 8, 2014 (3 pages).

English translation of Japanese Office Action, Notice of Reasons for Rejection, Japanese Application No. 2011-553665. Dispatch Date: Apr. 8, 2014 (4 pages).

International Search Report for corresponding International Application No. PCT/JP2010/006661 mailed Jan. 11, 2011.

Form PCT/ISA/237 for corresponding International Application No. PCT/ JP2010/006661 dated Jan. 11, 2011 and Partial English translation.

Stein et al., "Use of Carotid Ultrasound to Identify Subclinical Vascular Disease and Evaluate Cardiovascular Disease Risk: A Consensus Statement from the American Society of Echocardiography Carotid Intima-Media Thickness Task Force", Journal of the American Society of Echocardiography, vol. 21, Issue 2, Feb. 2008, pp. 93-111 (cited in [0003] of the specification).

Office Action dated Mar. 30, 2015 for the corresponding Chinese Patent Application No. CN201080036008.3 (3 pages).

English translation of Office Action dated Mar. 30, 2015 for the corresponding Chinese Patent Application No. CN201080036008.3 (9 pages).

The Extended European Search Report dated Jul. 17, 2015 issued from the corresponding European Application No. 10845708.6.

* cited by examiner

FIG.3
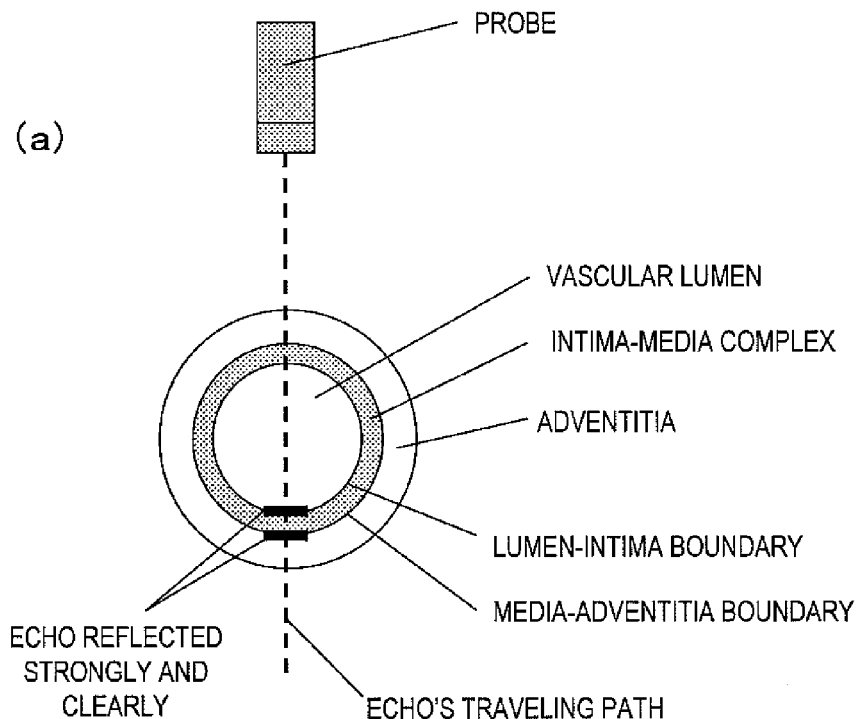
(a)
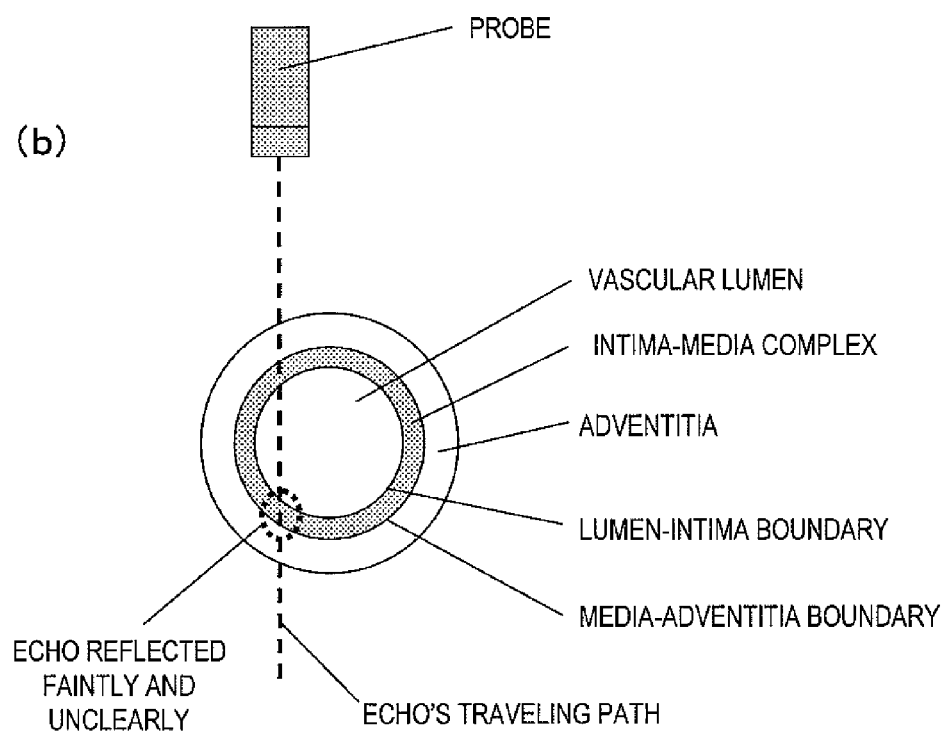
(b)

FIG. 7
(a)
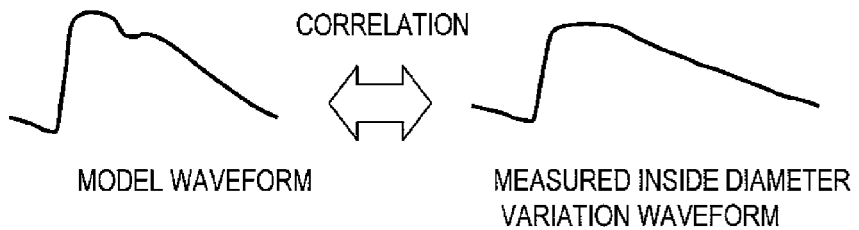
(b)
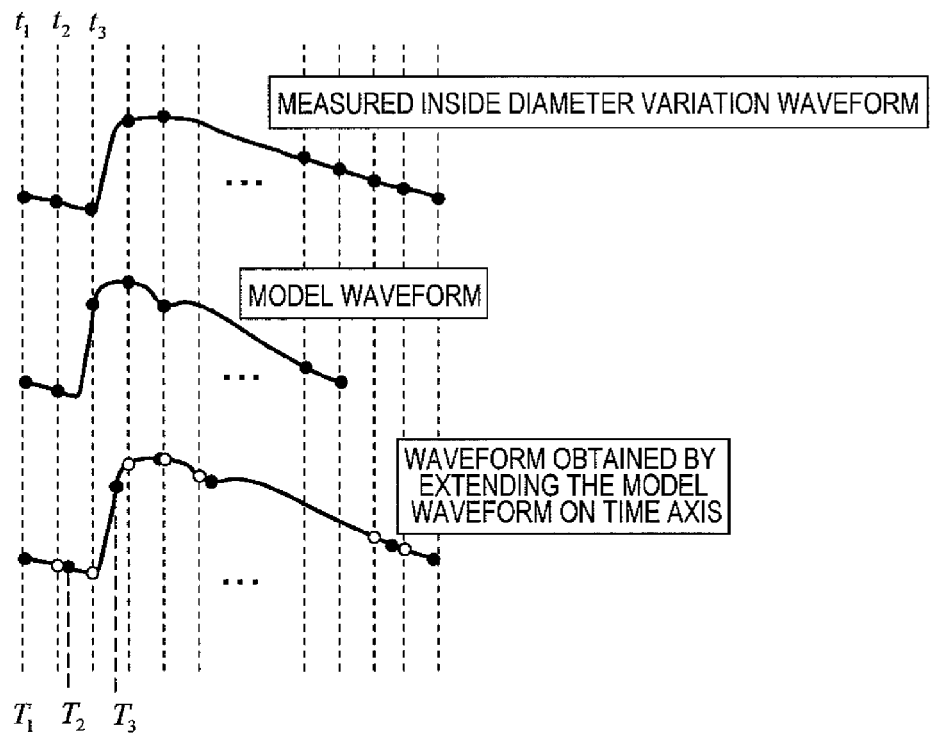

FIG.8
(a)
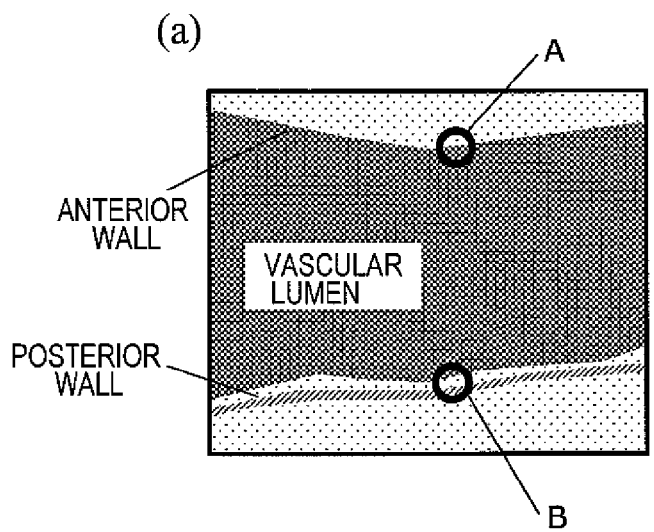
(b)

ULTRASONIC DIAGNOSTIC DEVICE, AND METHOD FOR MEASURING INITMA-MEDIA COMPLEX THICKNESS

TECHNICAL FIELD

The present invention relates to an ultrasonic diagnostic apparatus and a method for measuring an intima-media thickness using the apparatus.

BACKGROUND ART

In making a diagnosis of arterial sclerosis using an ultrasonic diagnostic apparatus, the intima-media complex thickness (which will be abbreviated herein as "IMT") of a carotid artery is known as one of most important indices to the status of an initial atherosclerosis. The IMT means the thickness of an intima-media complex in the vascular wall of a carotid artery. As shown in FIG. 18, the intima-media complex is a layer that is visible between the vascular lumen and the adventitia. And when making an inspection, the boundary between the vascular lumen and the intima (which will be referred to herein as a "lumen-intima boundary") and the boundary between the media and the adventitia (which will be referred to herein as a "media-adventitia boundary") are detected and the thickness between them is measured. A method for automatically measuring the IMT is disclosed in Patent Document No. 1, for example.

In general, when the IMT is measured, an IMT measuring range is set along the carotid artery and the maximum thickness (max IMT) or mean thickness (mean IMT) is measured within that range as shown in FIG. 18. For example, Non-Patent Document No. 1 recommends that such an IMT measuring range have a length of 1 cm.

CITATION LIST

Patent Literature

Patent Document No. 1: Japanese Patent Application Laid-Open Publication No. 2008-168016

Non-Patent Literature

Non-Patent Document No. 1: Journal of the American Society of Echocardiography, February 2008 (pp. 93 to 111)

SUMMARY OF INVENTION

Technical Problem

If the status of a carotid artery, which is the object of inspection, is going to be checked using a conventional ultrasonic diagnostic apparatus, however, nobody but a well experienced skilled person could make an accurate measurement, which is a problem with the prior art.

The reason is that to check the status of a carotid artery using a conventional apparatus, the probe should be put exactly at a position where the centerline of the carotid artery can be cut vertically.

Also, even if an image that would allow the person to check the status of the carotid artery accurately has come up successfully by putting the probe at a proper position, it is still never easy for him or her to get the measurement done accurately with the probe kept at that proper position. This is because he or she has to hold it in his or her hand to operate it.

Furthermore, as the blood flow running through the carotid artery changes its rate with the heartbeat, the diameter or thickness of the carotid artery also changes without a break. That is why even when the operator holds and puts the probe at a right position, it is not always the best timing to check the status of the carotid artery.

It is therefore an object of the present invention to get the status of a carotid artery checked without losing the best timing once the probe has been put at the right position to carry out the measurement.

Solution to Problem

An ultrasonic diagnostic apparatus according to the present invention, to which a probe with a transducer is connectible, includes: an ultrasonic signal processing section, which performs transmission processing for transmitting an ultrasonic wave toward a subject's blood vessel by driving the probe and also performs reception processing for generating a received signal based on the ultrasonic wave that has been reflected from the subject's blood vessel and received at the probe; a tomographic image processing section, which generates a tomographic image based on the received signal; a boundary detecting section, which detects the lumen-intima and media-adventitia boundaries of the blood vessel based on either the received signal or the tomographic image; a vascular wall thickness calculating section, which calculates, as a vascular wall thickness value, the interval between the lumen-intima and media-adventitia boundaries that have been detected by the boundary detecting section; a reliability determining section, which determines the reliability of the vascular wall thickness value by either a signal feature of the received signal or an image information feature of the tomographic image at a location on any of the lumen-intima and media-adventitia boundaries that have been detected; and a control section, which decides, in accordance with the decision made by the reliability determining section, that the vascular wall thickness value be defined as an intima-media thickness. According to this configuration, the IMT can be measured in an appropriate measuring state and a highly reliable result of measurement can be obtained.

In one preferred embodiment, the signal feature includes at least one of a signal intensity and a signal intensity distribution. According to this configuration, the reliability of the IMT value can be determined by either the signal intensity of the received signal or its signal intensity distribution. As a result, the IMT can be measured in an appropriate measuring state and a highly reliable result of measurement can be obtained.

In another preferred embodiment, the image information feature includes at least one of a luminance, a luminance distribution and a shape. According to this configuration, the reliability of the IMT value can be determined by either the luminance of the tomographic image, its luminance distribution or its form. As a result, the IMT can be measured in an appropriate measuring state and a highly reliable result of measurement can be obtained.

In still another preferred embodiment, the ultrasonic diagnostic apparatus further includes a vascular center determining section, which determines whether or not the received signal has been obtained from around a cross section of the blood vessel that passes its longitudinal center or which calculates an estimated value indicating the probability that the received signal has been obtained from around the cross section of the blood vessel that passes its longitudinal center, by either the signal feature of the received signal or the image information feature of the tomographic image at the location on the lumen-intima or media-adventitia boundary that has been detected. If the vascular center determining section has decided that the received signal have been obtained from around the cross section of the blood vessel that passes its longitudinal center or if the estimated value is beyond a predetermined reference value, the reliability determining section decides that the vascular wall thickness value have a high reliability or the reliability determining section decides that the higher the estimated value, the higher the reliability of the vascular wall thickness value. According to this configuration, by determining whether or not the received signal has been obtained from around a cross section of the blood vessel that passes its longitudinal center, it can be seen if an appropriate measuring state has been established. Consequently, a highly reliable result of measurement can be obtained.

In this particular preferred embodiment, the vascular center determining section evaluates if there is a signal intensity or luminance distribution that is unique to the lumen-intima and media-adventitia boundaries on either the received signal or the image information of the tomographic image representing the lumen-intima and media-adventitia boundaries that have been detected, thereby determining whether or not the received signal has been obtained from around the cross section of the blood vessel that passes its longitudinal center. According to this configuration, it can be decided properly that the received signal has been obtained from around a cross section of the blood vessel that passes its longitudinal center. Consequently, a highly reliable result of measurement can be obtained.

In a specific preferred embodiment, if there is a signal intensity or luminance distribution that is unique to the lumen-intima and media-adventitia boundaries on either the received signal or the image information of the tomographic image representing the lumen-intima and media-adventitia boundaries that have been detected, then the vascular center determining section estimates the length of a range where there is the signal intensity or luminance distribution, thereby determining whether or not the received signal has been obtained from around the cross section of the blood vessel that passes its longitudinal center. According to this configuration, it can be decided more properly that the received signal has been obtained from around a cross section of the blood vessel that passes its longitudinal center. Consequently, a highly reliable result of measurement can be obtained.

In still another preferred embodiment, the ultrasonic diagnostic apparatus further includes a pulsation detecting section, which checks the pulsating status of the blood vessel, thereby either determining whether the pulse of the blood vessel is being measured properly or calculating an estimated value indicating the probability that the pulse of the blood vessel is being measured properly. If the pulsation detecting section has decided that the pulse of the blood vessel be being measured properly or if the estimated value is beyond a predetermined reference value, the reliability determining section decides that the vascular wall thickness value have a high reliability or the reliability determining section decides that the higher the estimated value, the higher the reliability of the vascular wall thickness value. According to this configuration, by determining whether or not the pulse of the blood vessel is being measured properly, it can be seen if an appropriate measuring state has been established. Consequently, a highly reliable result of measurement can be obtained.

In this particular preferred embodiment, the pulsation detecting section checks the pulsating status of the blood vessel by sensing a variation in the inside diameter of the blood vessel and decides that the pulse of the blood vessel be being measured properly if the variation in the inside diameter of the blood vessel has a pulse waveform. According to this configuration, it can be decided properly that the pulse of the blood vessel be being measured properly. Consequently, a highly reliable result of measurement can be obtained.

In a specific preferred embodiment, the pulsation detecting section checks the pulsating status by detecting a feature quantity of the variation in the inside diameter of the blood vessel. According to this configuration, it can be decided more properly that the pulse of the blood vessel be being measured properly. Consequently, a highly reliable result of measurement can be obtained.

In an alternative preferred embodiment, the pulsation detecting section checks the pulsating status based on the correlation between a waveform representing the variation in the inside diameter of the blood vessel and a preregistered model waveform. According to this configuration, it can be decided more properly that the pulse of the blood vessel be being measured properly. Consequently, a highly reliable result of measurement can be obtained.

In yet another preferred embodiment, the pulsation detecting section includes a cardiac cycle detecting section that detects a particular timing during one cardiac cycle and that either determines whether or not the pulse of the blood vessel is being measured properly before and/or after the detected timing or calculates an estimated value indicating the probability that the pulse of the blood vessel is being measured properly before and/or after the detected timing. If the pulsation detecting section has decided that the pulse of the blood vessel be being measured properly before and/or after the detected timing or if the estimated value is beyond a predetermined reference value, the reliability determining section decides that the vascular wall thickness value have a high reliability or the reliability determining section decides that the higher the estimated value, the higher the reliability of the vascular wall thickness value. According to this configuration, the IMT that varies according to the cardiac rate can be measured exactly when the IMT becomes the maximum. Consequently, a highly reliable result of measurement can be obtained.

In this particular preferred embodiment, the pulsation detecting section checks the pulsating status by sensing a motion of the subject's tissue based on the received signal, and the cardiac cycle detecting section detects the particular timing during one cardiac cycle based on the pulsating status. According to this configuration, the IMT that varies according to the cardiac rate can be measured at the best timing without using any additional function such as an ECG. Consequently, a highly reliable result of measurement can be obtained easily and with good operability.

In an alternative preferred embodiment, the cardiac cycle detecting section detects the timing based on an electrocardiographic complex. According to this configuration, the end-diastolic timing can be detected accurately using an ECG. Consequently, a highly reliable result of measurement can be obtained.

In yet another preferred embodiment, the timing detected by the cardiac cycle detecting section is the end-diastolic timing. According to this configuration, the best timing to measure the IMT value appropriately can be determined by detecting the end-diastolic timing. Consequently, a highly reliable result of measurement can be obtained.

In yet another preferred embodiment, the timing detected by the cardiac cycle detecting section is later than the end-diastolic timing by a predetermined amount of time. According to configuration, the exact timing when the IMT value becomes the maximum in a predetermined time after the end of the diastolic phase can be detected. Consequently, a highly reliable result of measurement can be obtained.

In yet another preferred embodiment, the ultrasonic diagnostic apparatus further includes a longitudinal axis determining section that either determines whether or not the received signal or the tomographic image covers a longitudinal cross section of the subject's blood vessel or calculates an estimated value indicating the probability that the received signal or the tomographic image covers a longitudinal cross section of the subject's blood vessel. If the longitudinal axis determining section has decided that the received signal or the tomographic image covers a longitudinal cross section of the subject's blood vessel or if the estimated value is beyond a predetermined reference value, the reliability determining section decides that the vascular wall thickness value have a high reliability or the reliability determining section decides that the higher the estimated value, the higher the reliability of the vascular wall thickness value. According to this configuration, by determining whether or not the received signal or the tomographic image covers a longitudinal cross section of the blood vessel, it can be seen if an appropriate measuring state has been established. Consequently, a highly reliable result of measurement can be obtained.

In yet another preferred embodiment, the ultrasonic diagnostic apparatus further includes a stability determining section that either determines, by the magnitude of invariability of the vascular wall thickness value with time, whether or not the vascular wall thickness value is a stabilized one or calculates, based on the magnitude of invariability of the vascular wall thickness value with time, the probability that the vascular wall thickness value is a stabilized one. If the stability determining section has decided that the vascular wall thickness value is a stabilized one, the reliability determining section decides that the vascular wall thickness value have a high reliability. Or if the estimated value is beyond a predetermined reference value, the reliability determining section decides that the more removed the estimated value, the higher the reliability of the vascular wall thickness value. According to this configuration, by determining, by the magnitude of invariability of the vascular wall thickness value with time, whether or not the vascular wall thickness value is a stabilized one, it can be seen if an appropriate measuring state has been established. Consequently, a highly reliable result of measurement can be obtained.

In yet another preferred embodiment, the ultrasonic diagnostic apparatus further includes an image synthesizing section that synthesizes together the decision made by the reliability determining section and the tomographic image generated by the tomographic image processing section, and a synthetic image obtained by the image synthesizing section is displayed. According to this configuration, it can be seen visually if an appropriate measuring state has been established, and therefore, the operator can confirm the result of measurement and its reliability with his or her own eyes. As a result, the operability increases.

In yet another preferred embodiment, the ultrasonic diagnostic apparatus further includes a decision criterion setting section that sets, by reference to the received signal obtained from the subject's blood vessel or information about the tomographic image generated by the tomographic image processing section and the boundary detected by the boundary detecting section, a criterion of decision for use to perform the vascular center determining process, the pulsating status checkout process, the longitudinal axis determining process or the stability determining process. According to this configuration, the vascular center determining process, the pulsating status checkout process, the longitudinal axis determining process and the stability determining process can be carried out according to the attribute of the subject's tissue. As a result, the IMT measured value can be a more accurate and more reliable one.

In yet another preferred embodiment, the ultrasonic signal processing section performs the transmission processing and the reception processing a number of times, thereby sequentially generating multiple received signals. The tomographic image processing section sequentially generates multiple tomographic images based on the multiple received signals. The boundary detecting section sequentially detects the lumen-intima and media-adventitia boundaries of the blood vessel based on each of the multiple received signals or each of the multiple tomographic images. The vascular wall thickness calculating section sequentially calculates the vascular wall thickness values based on the lumen-intima and media-adventitia boundaries of the blood vessel that have been detected sequentially. The reliability determining section sequentially determines the degrees of reliability of the vascular wall thickness values that have been calculated sequentially. The control section decides, in accordance with the decision made by the reliability determining section, that the vascular wall thickness value be defined as an intima-media thickness. And at least the tomographic images generated sequentially are displayed.

In this particular preferred embodiment, in accordance with the decision made by the reliability determining section, the control section freezes the tomographic images that are displayed sequentially. According to this configuration, the image displayed when the IMT is measured appropriately can be frozen.

In another preferred embodiment, the ultrasonic diagnostic apparatus further includes a frame storage section, which sequentially stores, as frames, the tomographic images, the vascular wall thickness values and the decision made by the reliability determining section, and a best frame choosing section, which chooses a frame with the highest reliability from either all or a subset of the frames that have been stored in the frame storage section. The control section decides that the vascular wall thickness value calculated by the vascular wall thickness calculating section on the frame that has been chosen by the best frame choosing section be defined as the intima-media thickness. According to this configuration, the IMT value obtained can be reliable enough to use as the result of measurement.

In this particular preferred embodiment, if at least a certain number of frames, of which the vascular wall thickness values have degrees of reliability that are higher than a predetermined value, have been written in the frame storage section, the control section freezes the tomographic images that are displayed sequentially. According to this configuration, when the IMT value obtained is a highly reliable one, the image displayed then can be frozen.

In another preferred embodiment, when the number of frames, of which the vascular wall thickness values have degrees of reliability that are higher than a predetermined value and which have been written consecutively in the frame storage section, reaches a particular number, the control section freezes the tomographic images that are displayed sequentially. According to this configuration, when the IMT value obtained is a highly reliable one, the image displayed then can be frozen.

In this particular preferred embodiment, the best frame choosing section chooses a frame with the highest degree of reliability from the particular number of frames, of which the degrees of reliability are higher than the predetermined value and which have been written consecutively in the frame storage section. According to this configuration, the IMT measured value can be an even more reliable one.

A method for measuring an intima-media thickness according to the present invention includes the steps of: performing reception processing for generating a received signal based on an ultrasonic wave that has been reflected from a subject's blood vessel and received at a probe; generating a tomographic image based on the received signal; detecting the lumen-intima and media-adventitia boundaries of the blood vessel based on either the received signal or the tomographic image; calculating, as a vascular wall thickness value, the interval between the lumen-intima and media-adventitia boundaries that have been detected; determining the reliability of the vascular wall thickness value by either a signal feature of the received signal or an image information feature of the tomographic image at a location on any of the lumen-intima and media-adventitia boundaries that have been detected; and deciding, in accordance with the result obtained, that the vascular wall thickness value should be regarded as the intima-media thickness. According to this method, the IMT value can be measured in an appropriate measured state and can be a highly reliable one.

Another method for measuring an intima-media thickness according to the present invention includes the steps of: performing reception processing for generating a received signal based on an ultrasonic wave that has been reflected from a subject's blood vessel and received at a probe; generating a tomographic image based on the received signal; detecting the lumen-intima and media-adventitia boundaries of the blood vessel based on either the received signal or the tomographic image; calculating, as a vascular wall thickness value, the interval between the lumen-intima and media-adventitia boundaries that have been detected; checking the pulsating status of the blood vessel; determining, by either a signal feature of the received signal or an image information feature of the tomographic image at a location on the lumen-intima and/or media-adventitia boundaries that have been detected, whether or not the received signal has been obtained from around a cross section of the blood vessel that passes its center in a longitudinal direction; determining, based on the pulsating status of the blood vessel checked, whether the pulse of the blood vessel is being measured properly; determining the reliability of the vascular wall thickness value based on the decision made on whether the received signal has been obtained from around the cross section of the blood vessel that passes its longitudinal center and the decision made on whether the pulse of the blood vessel is being measured properly; and deciding, in accordance with the decision made, that the vascular wall thickness value calculated be defined as the intima-media thickness. According to this configuration, the best timing to measure the IMT value appropriately can be detected more accurately. As a result, the IMT value can be measured in an even more appropriate state and an even more reliable result of measurement can be obtained.

Advantageous Effects of Invention

According to the ultrasonic diagnostic apparatus and IMT measuring method of the present invention, just by confirming that the two boundaries between the lumen and the intima and between the media and the adventitia have been detected successfully and that the pulse of the blood vessel is being measured properly, it can be determined whether the blood vessel that is the object of IMT measurement is inspected in an appropriate state (e.g., whether the probe is put in a right position). And the IMT value that has been measured at the very best timing during one cardiac cycle is used as the final result of measurement. As a result, the IMT value thus obtained can be a highly reliable one, thus contributing to significantly increasing the accuracy and operability of the inspection of arterial sclerosis, among other things.

BRIEF DESCRIPTION OF DRAWINGS

FIG. 3(a) illustrates how lumen-intima and media-adventitia boundaries will be rendered if the blood vessel is scanned successfully from right over its center, and FIG. 3(b) illustrates how the lumen-intima and media-adventitia boundaries will be rendered if the blood vessel is failed to be scanned from right over its center.

FIG. 7(a) illustrates a correlation between a model waveform and the inside diameter variation waveform of the carotid artery and FIG. 7(b) illustrates how to extend or shorten the model waveform on the time axis.

FIG. 8(a) illustrates the structure of a carotid artery under inspection and FIG. 8(b) shows the inside diameter variation waveform of the carotid artery and the end-diastolic timing.

DESCRIPTION OF EMBODIMENTS

Embodiment 1

Figure 1:
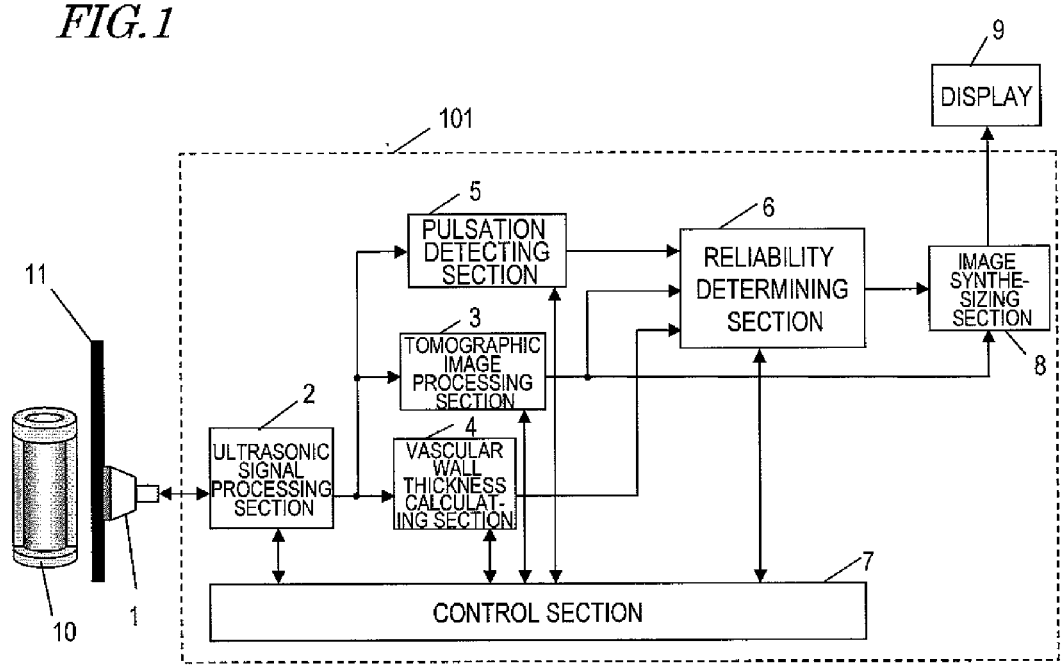
FIG. 1 is a block diagram illustrating an ultrasonic diagnostic apparatus as a first specific preferred embodiment of the present invention.

FIG. 1 is a block diagram illustrating an ultrasonic diagnostic apparatus as a first specific preferred embodiment of the present invention. The ultrasonic diagnostic apparatus 101 of the first preferred embodiment includes an ultrasonic signal processing section 2, a tomographic image processing section 3, a vascular wall thickness calculating section 4, a pulsation detecting section 5, a reliability determining section 6, a control section 7 and an image synthesizing section 8.

A probe 1 includes an ultrasonic transducer and transmits an ultrasonic wave toward a subject, and receives the ultrasonic wave that has been reflected from the subject and converts it into an electrical signal, through the ultrasonic transducer. The ultrasonic signal processing section 2 is designed so that the probe 1 is readily attachable to, and removable from, it and performs transmission processing by driving the ultrasonic transducer of the probe 1 with a drive pulse applied thereto at a predetermined timing to make the probe 1 send out an ultrasonic wave. The ultrasonic signal processing section 2 also receives an electrical signal from the probe 1 and performs reception processing that should be done to generate an ultrasonic tomographic image by amplifying and detecting the electrical signal, thereby generating a received signal.

The ultrasonic signal processing section 2 ordinarily performs the transmission processing continuously a number of times, thereby generating received signals sequentially. That is why the processing to be described below is performed sequentially on the received signals thus generated.

The tomographic image processing section 3 receives the received signals that have been generated by the ultrasonic signal processing section 2 and performs coordinate transformation and other kinds of processing on the received signals, thereby sequentially generating tomographic images as two-dimensional ultrasonic images. The vascular wall thickness calculating section 4 calculates the thickness of the wall of the subject's blood vessel that is the object of measurement. The pulsation detecting section 5 checks the pulsating status of the blood vessel and determines whether or not the pulse of the blood vessel is being measured properly.

In calculating the thickness of the vascular wall that is the object of measurement, the reliability determining section 6 determines, based on the results obtained by the tomographic image processing section 3, the vascular wall thickness calculating section 4 and the pulsation detecting section 5, whether or not the status being checked and the calculated values are reliable enough to be final ones.

The control section 7 controls the respective blocks and either decides that the result of measurement that has already had its reliability determined by the reliability determining section 6 be regarded and saved as the intima-media thickness measured or freezes the image at the point in time when such a result of measurement is obtained.

The image synthesizing section 8 is designed so as to be connectible to the display 9 and synthesizes together the result obtained by the reliability determining section 6 and the tomographic image generated by the tomographic image processing section 3 so that the synthetic image thus obtained can be presented on the display 9 connected. The display 9 is a monitor that is connected to the image synthesizing section 8 and that displays its image signal thereon.

Next, the ultrasonic diagnostic apparatus of this first preferred embodiment will be described in further detail with reference to FIG. 2, which is a block diagram illustrating a more detailed configuration of this apparatus. As FIG. 2 just illustrates details of the configuration shown in FIG. 1, the blocks that have already been described with reference to FIG. 1 will not be described all over again if not necessary.

The vascular wall thickness calculating section 4 includes a boundary detecting section 41 and an IMT calculating section 42. The boundary detecting section 41 detects the two boundaries of the blood vessel under measurement (i.e., its lumen-intima boundary and media-adventitia boundary) in a range including the IMT measuring range (see FIG. 18). The IMT calculating section 42 calculates, as the IMT, the distance between the lumen-intima and media-adventitia boundaries that have been detected by the boundary detecting section 41. In this case, max IMT is calculated as the IMT if the maximum distance in the IMT measuring range is adopted but mean IMT is calculated as the IMT if the mean distance in the IMT measuring range is adopted. However, these are only examples of the present invention.

A vascular center determining section 31 receives the tomographic image that has been generated by the tomographic image processing section 3 and the vascular boundaries that have been detected by the boundary detecting section 41 and evaluates if the lumen-intima and media-adventitia boundaries are rendered clearly at those vascular boundary locations on the tomographic image or estimates the lengths of portions of the tomographic image where the lumen-intima and media-adventitia boundaries are rendered clearly, thereby determining whether or not the probe 1 put on the subject 1 now is located right over the center of the blood vessel that is the object of measurement.

The pulsation detecting section 5 includes a pulsation information processing section 51, a pulsating status checking section 52 and a cardiac cycle detecting section 53. The pulsation information processing section 51 processes the received signals that have been generated by the ultrasonic signal processing section 2, thereby extracting information from them in order to determine whether or not the blood vessel under measurement is pulsating. The pulsating status checking section 52 determines, based on the information that has been processed and extracted by the pulsation information processing section 51, whether or not the blood vessel is pulsating. The cardiac cycle detecting section 53 detects a particular timing during one cardiac cycle (e.g., the end of the diastolic phase that is a time when the heart that has contracted dilates to make the amount of the blood flow smallest).

Hereinafter, conditions for measuring the IMT value accurately and with good reproducibility will be described.

First of all, as the blood vessel has a substantially round cross section, it should be determined whether or not the probe 1 put on the subject is located right over around the center of the blood vessel (i.e., around the center of the circle so to speak) in order to measure the thickness of the vascular wall accurately. This is because in order to calculate the IMT value as the interval between the lumen-intima and media-adventitia boundaries of the blood vessel, both of these two boundaries of the blood vessel should be rendered clearly. And that decision is made by the vascular center determining section 31.

This point will be described in further detail with reference to FIG. 3, which is a schematic representation illustrating where the echo transmitted from, and received at, the probe 1 travels with respect to a cross section of the blood vessel.

Generally speaking, an echo is reflected from a boundary between two regions that have mutually different acoustic impedances. In this case, the closer to 90 degrees the angle of incidence defined by the echo with respect to the boundary, the more strongly the echo will be reflected and the clearer the reflected echo signal will be. That is why if the probe 1 put on the subject is located right over around the center of the blood vessel as shown in FIG. 3(a) (i.e., if the echo travels right through the vicinity of the center of the blood vessel), the echo is incident perpendicularly onto the lumen-intima and media-adventitia boundaries of the blood vessel and strong and clear reflected echoes are obtained from both of the two boundaries.

On the other hand, if the echo does not travel through the vicinity of the center of the blood vessel as shown in FIG. 3(b), then the echo will not be incident perpendicularly onto the two boundaries and only faint and unclear reflected echoes are obtained after all. As a result, the lumen-intima and media-adventitia boundaries may be rendered as blurred and indistinct ones or the lumen-intima boundary may not be rendered at all.

That is why by seeing if the lumen-intima and media-adventitia boundaries are rendered clearly where those vascular boundaries should be located on the tomographic image, it can be determined whether the probe 1 put on the subject is located right over around the center of the blood vessel. In this case, the vicinity of the center where the two boundaries can be rendered clearly may be defined by the distance between the acoustic line of the ultrasonic wave transmitted from the probe 1 (as indicated by the dashed line in FIG. 3) and the center of the cross section of the blood vessel, which may be 0.5 mm or less when measured actually. But the distance should not always be exactly equal to that value.

Figure 18:
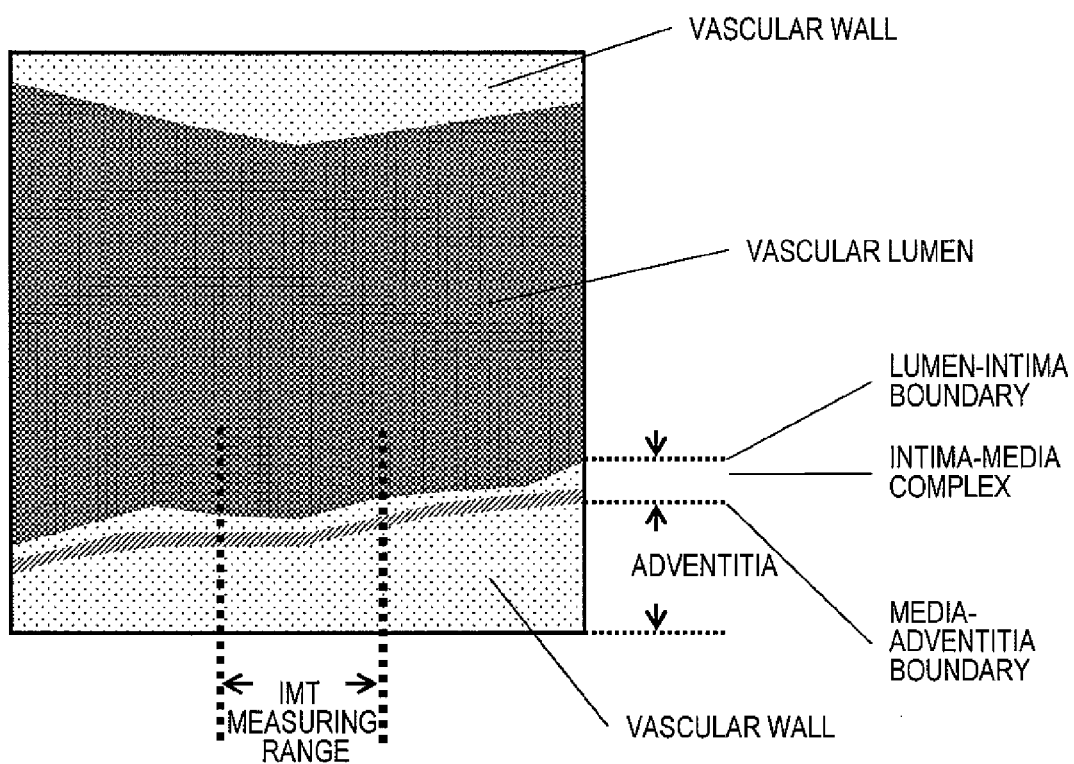
FIG. 18 illustrates the structure of the carotid artery under inspection and an IMT measuring range.

More specifically, by seeing if the tomographic image data representing the locations of the vascular boundaries detected and their surrounding sites has a portion in which the luminance rises from one side of the detected lumen-intima boundary closer to the vascular lumen toward the intima-media complex, or a portion in which the luminance rises from one side of the detected media-adventitia boundary closer to the intima-media complex toward the adventitia, or a portion in which the luminance falls between the lumen-intima and media-adventitia boundaries detected as shown in FIG. 18, it can be determined whether or not the lumen-intima and media-adventitia boundaries are rendered clearly at the vascular boundary locations on the tomographic image.

As described above, the length of a portion of the tomographic image in which the lumen-intima and media-adventitia boundaries are rendered clearly may also be used as a criterion to determine whether the probe 1 put on the subject is located right over around the center of the blood vessel. In that case, to make the decision, the two boundaries described above should be rendered clearly in preferably all, or at least a certain percentage, of the IMT measuring range (see FIG. 18). For example, if the IMT measuring range has a length of 1 cm and the certain percentage is 75%, then at least 7.5 mm out of the overall length of 1 cm should be usable to determine whether or not the blood vessel is caught properly around its center.

Secondly, the blood vessel will contract to varying degrees according to the volume or rate of the blood flow running inside itself. That is why when the heart is in the systolic phase, the blood flow rate becomes maximum, and the blood vessel comes to have the largest inside diameter and the smallest wall thickness. On the other hand, when the heart is in the diastolic phase, the blood flow rate becomes minimum, and the blood vessel comes to have the smallest inside diameter and the largest wall thickness. That is to say, since the vascular wall thickness varies synchronously with the heartbeat, the IMT value changes according to the timing of measurement.

Figure 4:
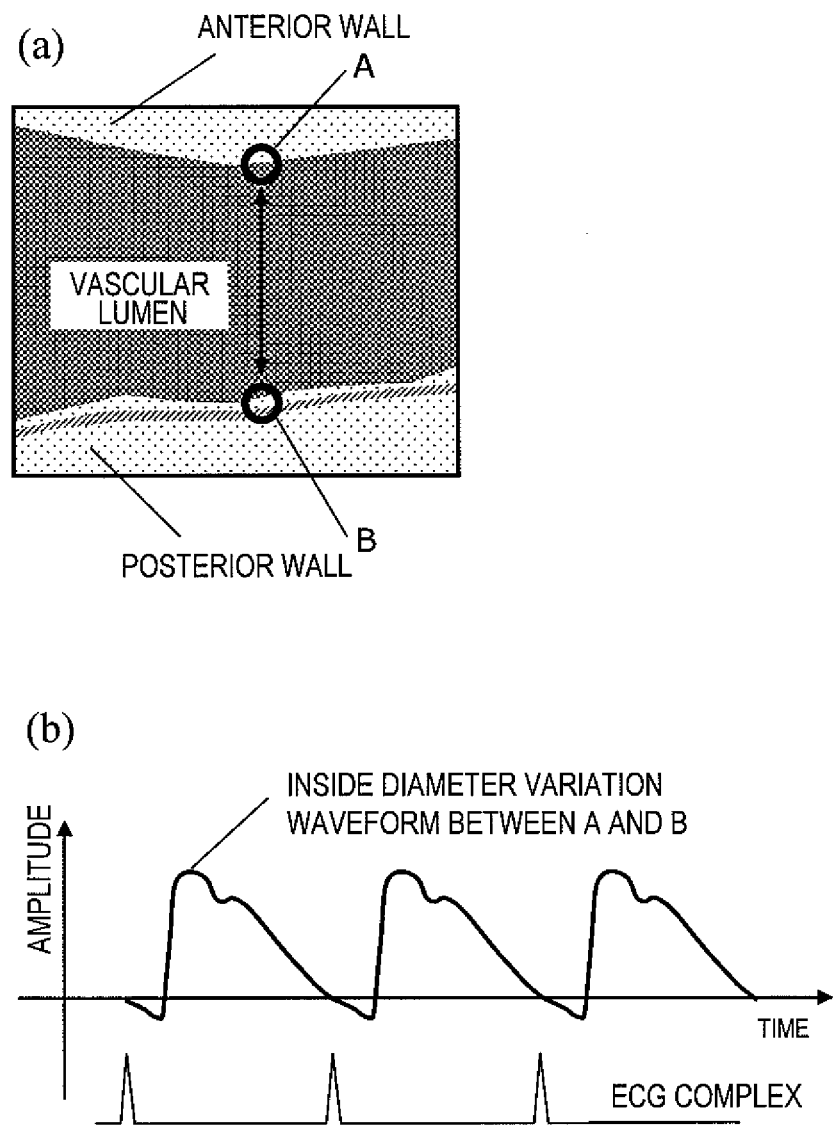
FIG. 4(a) illustrates the structure of a carotid artery under inspection and FIG. 4(b) shows the inside diameter variation waveform of the carotid artery.

This can be seen easily by reference to the drawings. As shown in FIG. 4, it is known that the distance between the two points A and B shown in FIG. 4(a) (i.e., the inside diameter of the blood vessel) varies with time as blood is pumped out of the heart, and therefore, the pulsed waveform such as the one shown in FIG. 4(b) is observed.

If an analysis is made by reference to the R-wave trigger timings of the ECG (as represented by the lower waveform shown in FIG. 4(b)), it can be seen that the inside diameter once decreases but increases steeply after that and then gradually returns to the original value. Speaking more strictly, in the case of a normal blood vessel, a peak called "dicrotic peak" is observed while the inside diameter is returning to the original value, and the inside diameter variation waveform has two positive peaks.

It is ideal to measure the IMT value when the vascular wall has the maximum thickness. That is why the best timing to measure the IMT should be determined with the heartbeat taken into account. And that timing is detected by the cardiac cycle detecting section 53.

Next, it will be described how to determine whether or the pulsating status is checked properly. When the thickness of the vascular wall is measured, it is necessary to see if the blood vessel is caught just as intended with the probe. Normally, in any organism, its blood vessel (and the artery, in particular) is always pulsating. That is why the pulsating status checking section 52 does not examine whether the blood vessel is pulsating, but determines whether or not the probe is put in a right position to get information about the blood vessel properly by seeing if the pulsation of the blood vessel is measured properly.

Figure 5:
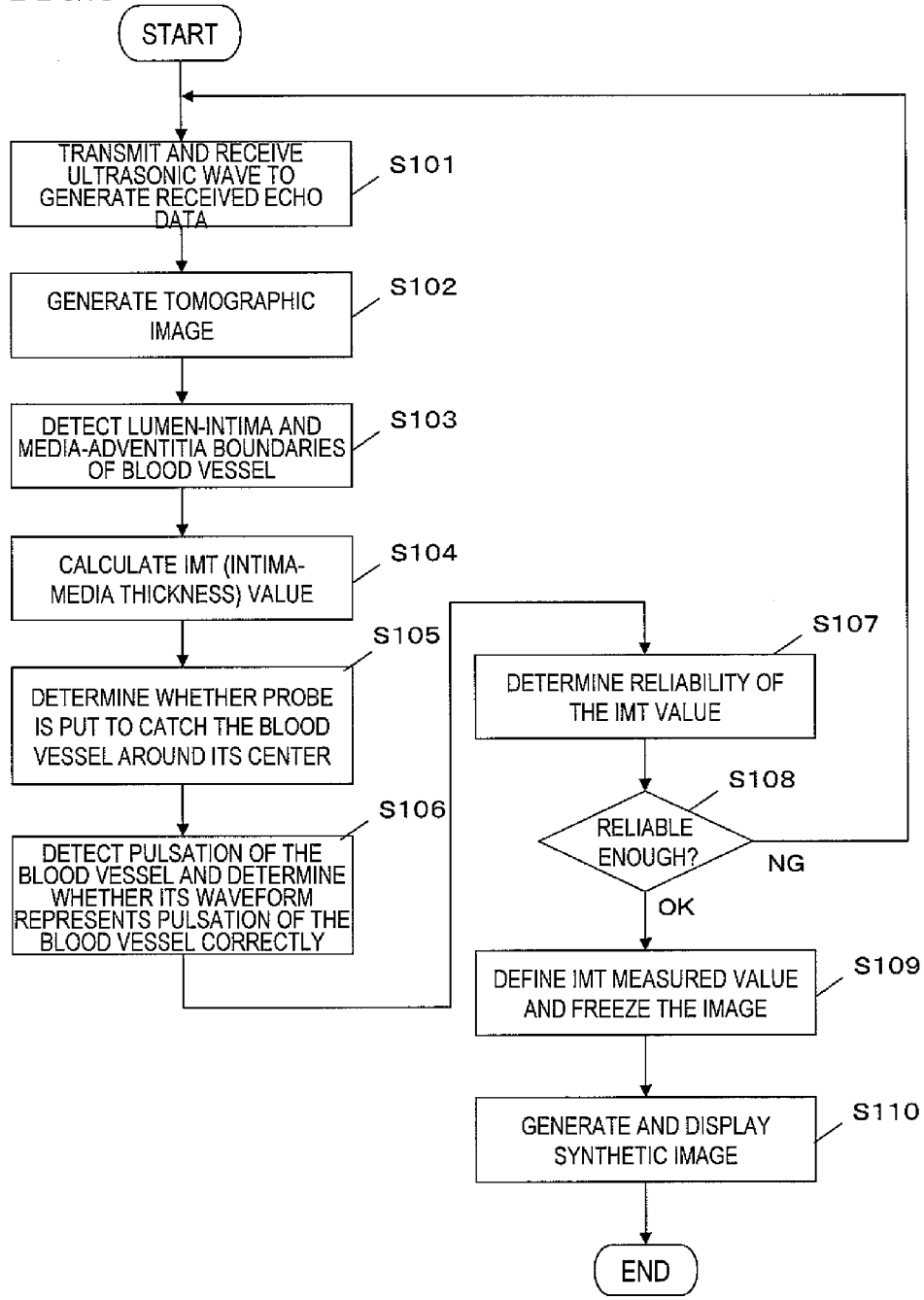
FIG. 5 is a flowchart showing a procedure of operation according to the first preferred embodiment.

Hereinafter, it will be described with reference to FIGS. 2 and 5 how the apparatus of this first preferred embodiment operates. FIG. 5 is a flowchart showing a typical procedure of operation according to the first preferred embodiment.

First of all, in Step S101, the ultrasonic signal processing section 2 performs transmission and reception controls on ultrasonic signals, thereby transmitting an ultrasonic wave with the probe 1 driven and receiving, at the probe 1, the ultrasonic wave that has been reflected form the subject. And just like a normal ultrasonic diagnostic apparatus, the ultrasonic signal processing section 2 performs ordinary signal processing on that reflected ultrasonic wave received to generate a received signal (received echo data).

Next, in Step S102, the tomographic image processing section 3 processes the received echo data, thereby generating a tomographic image. The tomographic image data generated in this processing step may be a subject's visceral organ or any of various other objects. In this example, however, an image representing the subject's blood vessel (and an image representing his or her artery, in particular) and its data are supposed to be processed mainly.

Meanwhile, the received echo data is also output from the ultrasonic signal processing section 2 to the vascular wall thickness detecting section 4 and the pulsation detecting section 5.

Subsequently, in Step S103, the boundary detecting section 41 of the vascular wall thickness detecting section 4 detects the lumen-intima and media-adventitia boundaries of the blood vessel based on the amplitude and phase of the received echo signal that has been supplied from the ultrasonic signal processing section 2.

This processing step is carried out on each measuring point in the region of interest (ROI) of the image that has been defined in advance. The ROI is normally defined so as to correspond with the IMT measuring range (see FIG. 18).

Thereafter, in Step S104, based on the location information of the lumen-intima and media-adventitia boundaries that have been detected by the boundary detecting section 41, the IMT calculating section 42 calculates the thickness of the intima-media complex (i.e., the IMT value).

Also, the boundary detecting section 41 provides the result of detection of the lumen-intima and media-adventitia boundaries of the blood vessel for the vascular center determining section 31. In response, in Step S105, the vascular center determining section 31 determines, based on the tomographic image provided by the tomographic image processing section 3 and the result of the boundary detection, whether or not the received signal representing the blood vessel being currently caught by the probe has been obtained from around the center of the blood vessel.

Meanwhile, the received signal is also output from the ultrasonic signal processing section 2 to the pulsation detecting section 5.

Next, in Step S106, the pulsation detecting section 5 checks the pulsating status of the blood vessel that is the object of measurement and determines whether or not its waveform represents the pulsation of the blood vessel correctly.

Specifically, first, the pulsation information processing section 51 sets measuring points A and B on the anterior and posterior walls of the blood vessel under measurement as shown in FIG. 4(a) and analyzes the amplitude and phase of the received echo data, thereby tracking the motion of the measuring points A and B. Since the artery contracts and dilates repeatedly as the heart beats, the distance between these measuring points A and B also varies periodically. That is why its periodic variation is detected as a waveform representing a variation in the inside diameter of the blood vessel as shown in FIG. 4(b).

In this manner, simply by putting a probe on the subject without making any special connection between an electrocardiograph and the subject, such a waveform representing the variation in the inside diameter of the blood vessel can be obtained easily.

Next, by seeing if this inside diameter variation waveform obtained by the pulsation information processing section 51 has a pulse waveform, the pulsating status checking section 52 determines whether or not the inside diameter variation waveform represents the pulsation of the blood vessel properly.

This decision can be made by (1) paying attention to a simple feature quantity of the inside diameter variation waveform or (2) examining how much the inside diameter variation waveform agrees with a reference (or model) waveform.

Figure 6:
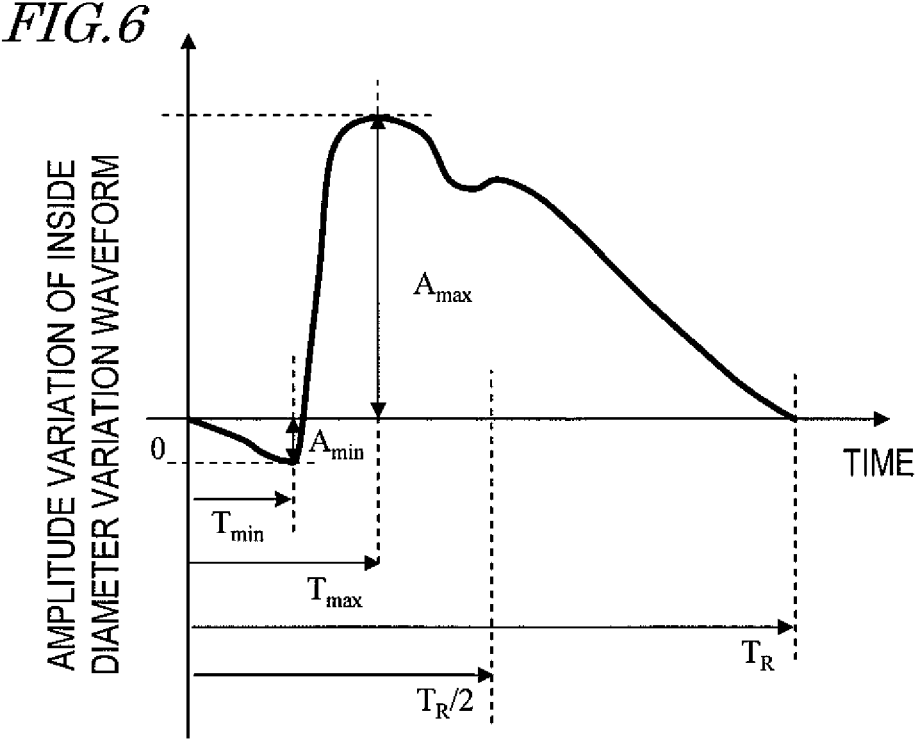
FIG. 6 shows exactly how the inside diameter of the carotid artery varies.

The method of (1) paying attention to a simple feature quantity of the waveform will be described with reference to FIG. 6. In that case, the pulsating status checking section 52 examines whether or not either the amplitude or a peak time falls within a normal human being's range. Examples of parameters of the feature quantity may include:

maximum and minimum amplitudes, which are respectively identified by Amax and Amin in FIG. 6;
time max when the amplitude becomes the maximum one Amax; and
time Tmin when the amplitude becomes the minimum one Amin
one cardiac cycle TR As for these parameters, the present inventors confirmed via experiments that if the waveform shown in FIG. 6 had an Amax of slightly less than 1 mm, a negative Amin value, and a TR of about 1 second and if Tmin<Tmax was satisfied, the pulsating status could be checked out.

Next, another method of (2) examining how much the inside diameter variation waveform agrees with a reference (or model) waveform will now be described with reference to FIG. 7.

First off, a reference model waveform is defined and the degree of matching between that waveform and the inside diameter variation waveform thus obtained is determined by calculating their correlation coefficient. In this case, the model waveform may be defined by collecting the data of the inside diameter waveforms of multiple persons.

More specifically, a coefficient representing the correlation between the model waveform and the inside diameter variation waveform thus obtained (which will be referred to herein as a "measured waveform") is calculated. If the model waveform and the measured waveform have mutually different time lengths, then the correlation coefficient may be calculated by extending or shortening the measured waveform along the time axis so that those two waveforms have the same time length. FIG. 7(b) illustrates a situation where the measured waveform has a longer time length than the model waveform. As one period (i.e., one cardiac cycle) of a model waveform disagrees in most cases with that of a subject's inside diameter variation waveform, the measured waveform should be extended or shortened as shown in FIG. 7(b) along the time axis.

The pulsating status may be checked out by using either only one of these two methods or both of them in combination. If only one of the two is adopted, the processing time can be shortened. On the other hand, if both methods are adopted, then the degree of matching between the two waveforms can be estimated more accurately.

This decision method is a waveform-based one. To obtain a more accurate IMT value, however, the timing of measurement is no less important as described above.

That is why the R-wave timing (representing the end-diastolic timing) should be detected.

With respect to the measuring points A and B that have been set on the anterior and posterior walls of the blood vessel that is the object of measurement, the cardiac cycle detecting section 53 detects the motion of the measuring point A with the heartbeat as a tracking waveform TA and obtains the magnitude of its variation as a differential waveform TA' as shown in FIG. 8. And this differential waveform TA' is regarded as representing a pseudo R wave timing and is stored as a waveform indicating the best time to measure the IMT.

As described above, it is a point in time around the end of one diastolic phase when the IMT value becomes maximum. That is why by detecting the point in time around the end of one diastolic phase, the IMT value can be measured at the best timing.

Figure 9:
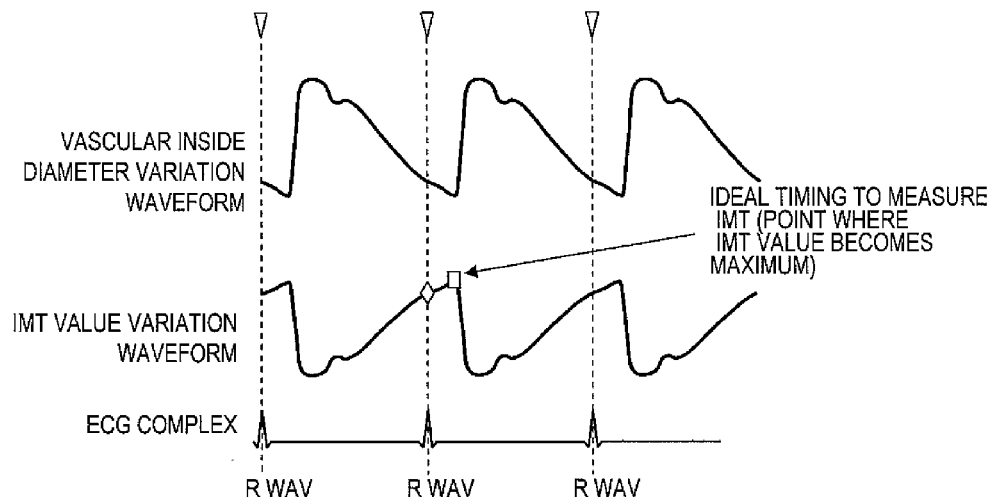
FIG. 9 illustrates a relation between the inside diameter variation waveform and the IMT value variation waveform of the blood vessel.

Strictly speaking, however, the ideal timing when the IMT value becomes maximum is later by a predetermined amount of time than the end of the diastolic phase (corresponding to the R wave timing on an electrocardiogram) as shown in FIG. 9. That is why by determining the time to measure the IMT value with that time delay taken into account, the measurement can get done with even more likelihood.

According to this method, the best time to measure the IMT can be detected even without using a device such as an ECG.

It should be noted that in one cardiac cycle, the best time to measure the IMT is not always the end of the diastolic phase but may also be set to be any other timing according to the processing time delay or processing method. Then, the apparatus of the present invention can be used even more universally.

Figure 10:
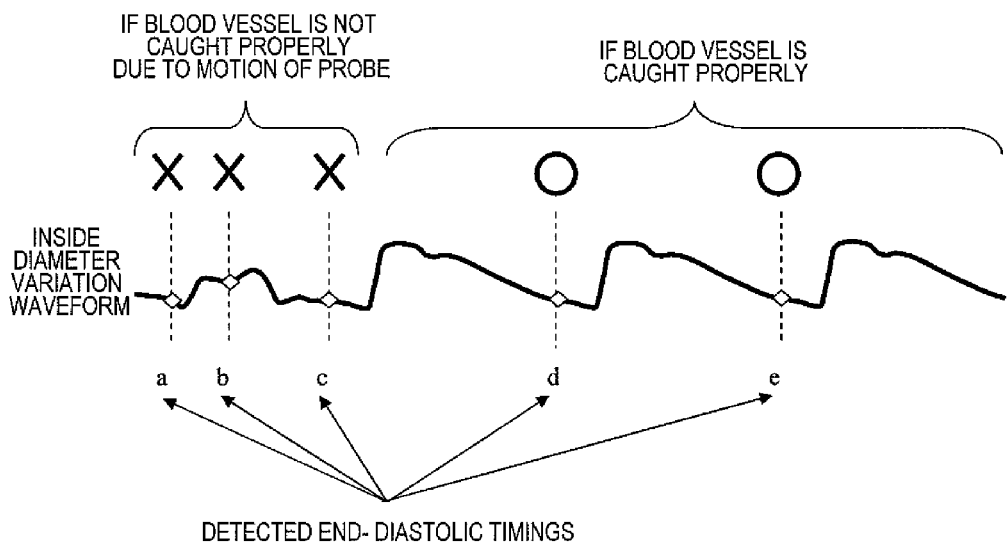
FIG. 10 illustrates a waveform representing both, a situation where the blood vessel is not being inspected properly and a situation where the blood vessel is being inspected properly.

FIG. 10 illustrates a waveform representing both a situation where the blood vessel is not being inspected properly and a situation where the blood vessel is being inspected properly.

In FIG. 10, the end of the diastolic phase is detected at respective points in time a through e. Among these points in time, the blood vessel is not caught properly at the former three points in time a, b and c but is caught properly at the latter two points in time d and e.

At the points in time d and e, the pulsating status has been checked out appropriately and the end of the diastolic phase has been detected properly by examining the inside diameter variation waveform. However, if a point in time that is not the end of the diastolic phase has been detected by mistake as at the points in time a, b and c due to an inappropriate movement of the probe during the inspection for the purpose of finding the blood vessel, then it can be seen, by examining the inside diameter variation waveform, that the blood vessel is not caught properly.

That is to say, the pulsating status checking section 52 makes reference to both the result of examination on the inside diameter variation waveform that has been obtained by the pulsation information processing section 51 and the time indicating the end of the diastolic phase that has been detected by the cardiac cycle detecting section 53, thereby deciding, with more accuracy, that the blood vessel is pulsating (i.e., the blood vessel is caught properly with the probe).

Finally, in Step S107, the reliability determining section 6 examines the pulsating status that has been detected and checked by the vascular center determining section 31 and the pulsation detecting section 5, thereby determining the reliability of the IMT value that has been calculated by the IMT calculating section 42. And in Step S108, the reliability determining section 6 determines whether the result of measurement is a reliable one or not. If the answer is YES, then the control section 7 decides that this IMT value be defined as the result of measurement. Otherwise, the process goes back to the processing step S101 to carry on the measurement.

Also, if it has been decided that the result of measurement be a reliable one, the reliability determining section 6 gets the processing of freezing the image done by the control section 7. In this manner, a highly reliable result of measurement and a tomographic image representing the blood vessel can be obtained as a result of the IMT measurement.

The reliability determining section 6 determines the reliability of the IMT value by examining whether or not the blood vessel as the object of inspection is being caught from a right angle to obtain an appropriate result of IMT measurement. And the decision is made based on the result obtained by the vascular center determining section 31 and the result obtained by the pulsating status checking section 52. More specifically, if the vascular center determining section 31 has decided that the probe 1 is put in a right position to catch the blood vessel around its center, the reliability determining section 6 regards the IMT value obtained as a highly reliable one. Likewise, if the pulsating status checking section 52 has decided that the pulse of the blood vessel be being measured properly, the reliability determining section 6 also regards the IMT value obtained as a highly reliable one. And if these two conditions are satisfied, the reliability determining section 6 decides that the IMT value obtained be reliable enough to use as the final result of measurement.

Alternatively, the vascular center determining section 31 may calculate an estimated value indicating the probability that the probe 1 is catching the blood vessel around its center. Meanwhile, the pulsating status checking section 52 may calculate an estimated value indicating the probability that the pulse of the blood vessel is being measured properly. Based on these estimated values that have been calculated by the vascular center determining section 31 and the pulsating status checking section 52, the reliability determining section 6 may calculate an estimated value indicating the reliability of the IMT value obtained. And if the estimated value is beyond a predetermined reference value, then the IMT value obtained may be regarded as being reliable enough. In this description, if "the estimated value is beyond a predetermined reference value", then the range of the values that are regarded as highly reliable ones may sometimes be greater than, and sometimes be less than, the reference value. That is to say, the highly reliable values may be greater than the reference value in some cases and may be less than the reference value in other cases. That is why depending on where the estimated value is set, the IMT value may be regarded as a reliable one sometimes when the estimated value is less than the reference value and sometimes when the estimated value is greater than the reference value. In any case, the IMT value is regarded as a reliable one as long as the estimated value falls within a predetermined range that has been set for the purpose of reliability determination.

In this case, the estimated value calculated by the vascular center determining section 31 may be set so that the greater the length of that portion of the tomographic image where the lumen-intima and media-adventitia boundaries are rendered clearly, the larger the estimated value or that the more steeply the luminance of the tomographic image rises or falls around the lumen-intima and media-adventitia boundaries detected, the larger the estimated value. Meanwhile, the estimated value calculated by the pulsating status checking section 52 may be set so that the greater the correlation between the model waveform and inside diameter variation waveform described above, the larger the estimated value.

In this case, the decision can be made based on either only the result obtained by the vascular center determining section 31 or just the one obtained by the pulsating status checking section 52. If both of these two results are relied on, the accuracy of the decision can be increased. Nevertheless, depending on the situation of the inspection, the decision can also be made based on only of those two results. That is why the given software programs may be selectively used appropriately according to the application, cost and weight of the apparatus.

Finally, in Step S110, the image synthesizing section 8 synthesizes together the IMT measured value, which has been regarded as the final result of measurement in accordance with the decision made by the reliability determining section 6, and the tomographic image that has been generated by the tomographic image processing section 3 and then outputs a synthetic image thus obtained to the display 9. As a result, the operator can confirm the diagnostic image and the result of measurement on the screen.

In the example illustrated in FIG. 5, the vascular center determining processing step S105 and the pulsating status checkout processing step S106 are supposed to be carried out in this order. However, these two processing steps may be performed in reverse order, too.

Also, in the preferred embodiment described above, the vascular center determining section 31 determines, based on the tomographic image that has been generated by the tomographic image generating section 3 and the vascular boundaries that have been detected by the boundary detecting section 41, whether or not the probe 1 is put in a right position to catch the blood vessel around its center just as intended. However, if the apparatus is designed so that the received echo signal is output from the ultrasonic signal processing section 2 directly to the vascular center determining section 31 without passing through the tomographic image processing section 3, the amplitude of the received echo signal supplied from the ultrasonic signal processing section 2 may be used instead of the tomographic image. In that case, the decision can be made without depending on the settings or parameters used when the tomographic image is generated.

Embodiment 2

Hereinafter, a second specific preferred embodiment of the present invention will be described with reference to FIG. 11. The typical procedure of operation of this second preferred embodiment is the same as what has already been described with reference to the flowchart of FIG. 5.

Figure 11:
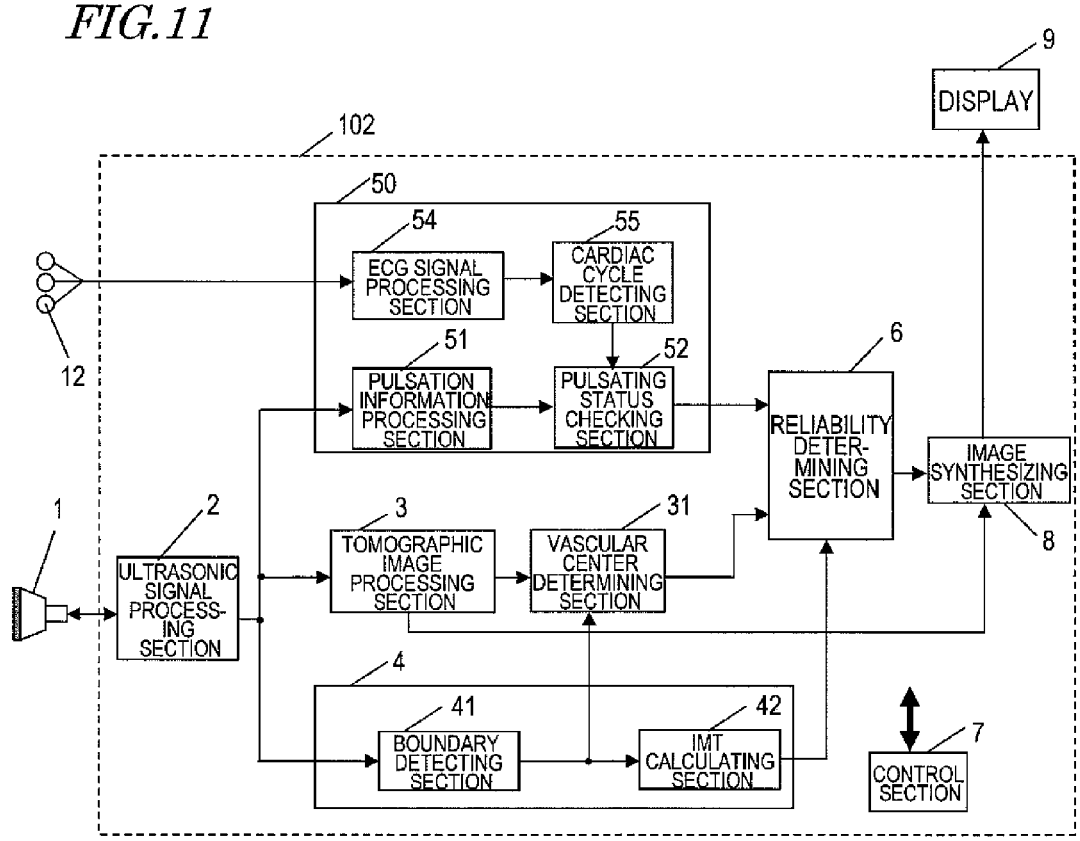
FIG. 11 is a block diagram illustrating a detailed configuration of an ultrasonic diagnostic apparatus as a second preferred embodiment of the present invention.

FIG. 11 is a block diagram illustrating an ultrasonic diagnostic apparatus as a second preferred embodiment of the present invention. The ultrasonic diagnostic apparatus 102 of this second preferred embodiment includes the ultrasonic signal processing section 2, the tomographic image processing section 3, the vascular wall thickness calculating section 4, a pulsation detecting section 50, the reliability determining section 6, the control section 7 and the image synthesizing section 8.

Figure 2:
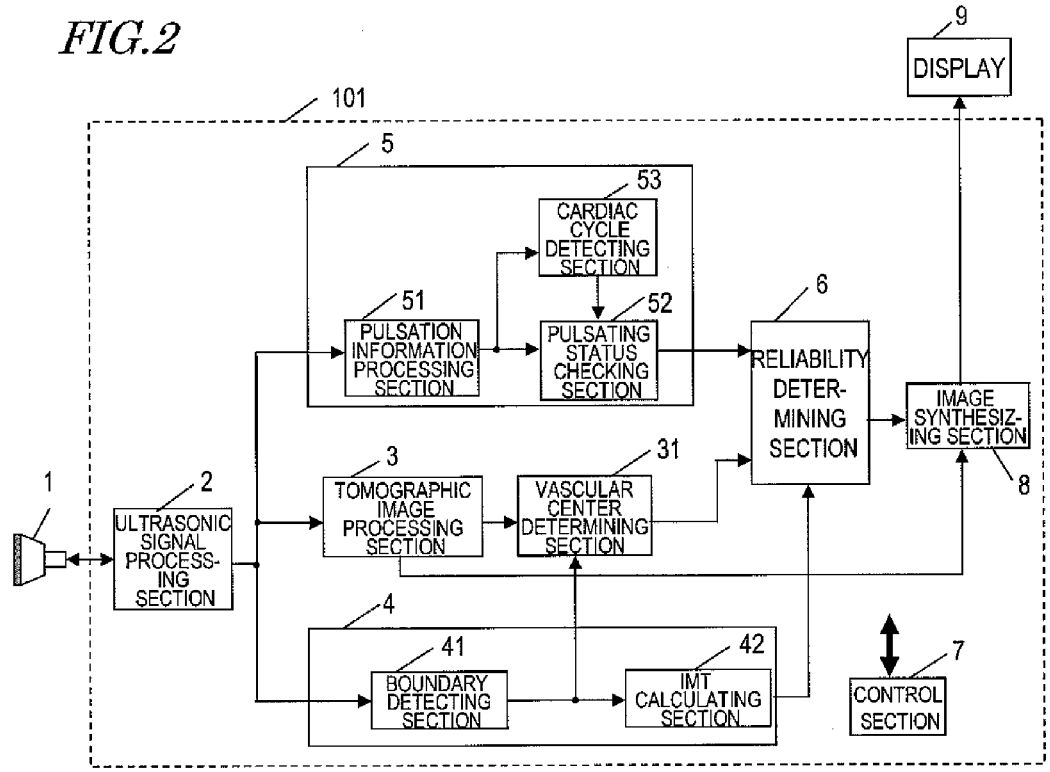
FIG. 2 is a block diagram illustrating a more detailed configuration of the first preferred embodiment of the present invention.

Unlike the apparatus of the first preferred embodiment illustrated in FIG. 2, the apparatus 102 of this preferred embodiment includes a pulsation detecting section 50 that includes the pulsation information processing section 51, the pulsating status checking section 52, an ECG signal processing section 54 and a cardiac cycle detecting section 55 instead of the pulsation detecting section 5.

The pulsation information processing section 51 and the pulsating status checking section 52 have the same configuration as their counterparts of the first preferred embodiment described above, and description thereof will be omitted herein.

Hereinafter, it will be described with reference to FIG. 11 how to detect the pulsation using an ECG. In the example illustrated in FIG. 11, the pulsation detecting section 50 includes the ECG signal processing section 54, which amplifies and analyzes the waveform of the subject's electrocardiogram signal that has been detected by an ECG pad 12, thereby detecting an R wave signal. Then, the cardiac cycle detecting section 55 detects the heartbeat timings based on the electrocardiogram signal analyzed by the ECG signal processing section 54. As already described for the first preferred embodiment, when the IMT is measured, the time when the IMT value becomes maximum is searched for by reference to the timing of the R wave indicating the end of the diastolic phase.

By using the ECG, the heartbeat timing, including the end of the diastolic phase, can be detected exactly, and therefore, the pulsating status can be checked out more accurately.

One of the major differences between the first and second preferred embodiments of the present invention is that an ECG is not used in the first preferred embodiment but is used in the second preferred embodiment. Compared to the configuration of the first preferred embodiment in which the end of diastolic phase detecting section 53 detects the end-diastolic timing indirectly based on a variation in the inside diameter of the blood vessel, the end of the diastolic phase can be detected more accurately according to this preferred embodiment because the electrocardiogram signal is monitored directly. Consequently, the IMT can be measured more accurately as well. Nevertheless, to obtain an ECG, the measurement should be made with ECG pads attached to the subject's wrists, ankles and chest, and therefore, the subject should lie down calm during the measurement.

On the other hand, since no EGC needs to be used according to the first preferred embodiment, the IMT can be measured just by putting an ultrasonic probe on the carotid artery at the patient's neck. As a result, compared to the measurement of the second preferred embodiment that uses an ECG, the measurement can get done more easily and more efficiently according to the first preferred embodiment.

That is to say, it is effective to adopt the method of the first preferred embodiment when the operability of measurement is given a higher priority and to employ the method of the second preferred embodiment when the accuracy of measurement should be increased.

More specifically, using the ultrasonic diagnostic apparatus with the configuration of the first preferred embodiment, inspection can be carried out easily or informally in order to detect any initial symptom of a cardiovascular disease. That is why the apparatus of the first preferred embodiment may be used when inspection needs to be made at some public place other than a hospital or a clinic (e.g., when a medical checkup needs to be carried out).

On the other hand, the ultrasonic diagnostic apparatus with the configuration of the second preferred embodiment may be used when a more accurate diagnosis of the condition of a cardiovascular disease needs to be made at a place fully equipped with dedicated medical devices.

Consequently, the present invention provides an ultrasonic diagnostic apparatus that can achieve both the effect of increasing the easiness and operability of IMT measurement during the inspection and the effect of increasing the accuracy of the IMT measurement.

Embodiment 3

Figure 12:
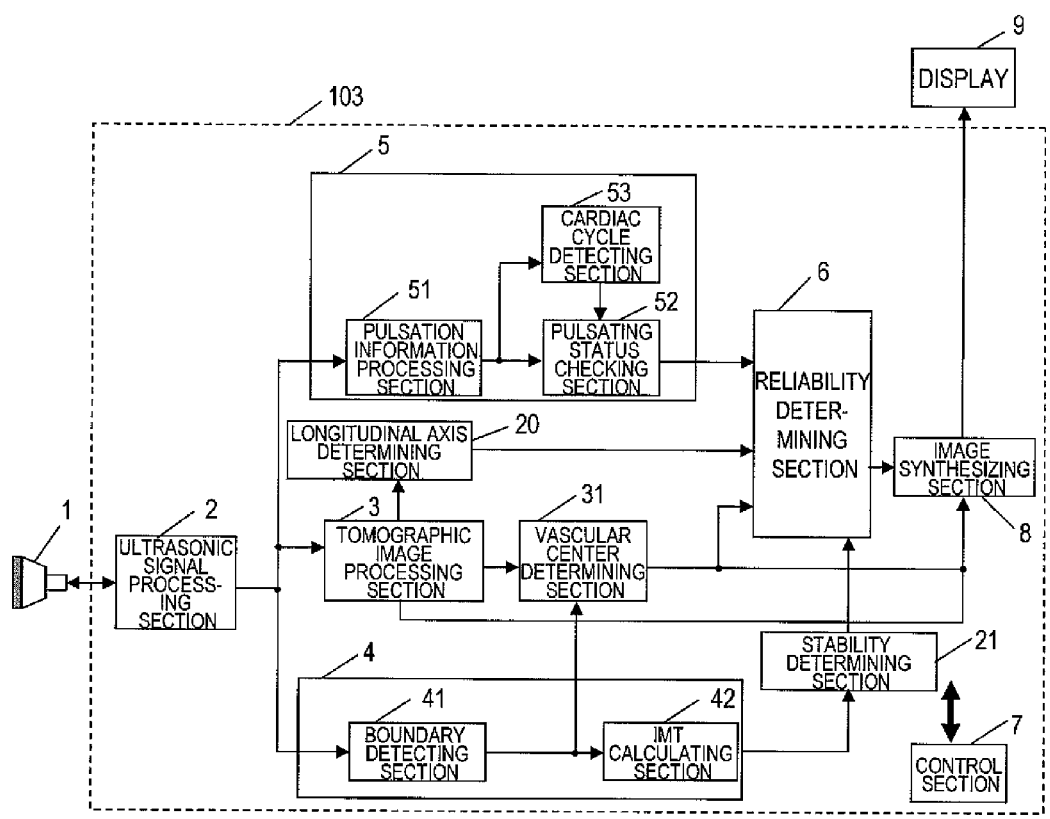
FIG. 12 is a block diagram illustrating a detailed configuration of an ultrasonic diagnostic apparatus as a third preferred embodiment of the present invention.

Hereinafter, a third specific preferred embodiment of the present invention will be described with reference to FIGS. 12 and 13, which are a block diagram illustrating an ultrasonic diagnostic apparatus as a third preferred embodiment of the present invention and a flowchart showing the typical procedure of operation according to the third preferred embodiment, respectively.

The ultrasonic diagnostic apparatus 103 of the third preferred embodiment of the present invention includes the ultrasonic signal processing section 2, the tomographic image processing section 3, the vascular wall thickness calculating section 4, the pulsation detecting section 5, the reliability determining section 6, the control section 7, the image synthesizing section 8, a longitudinal axis determining section 20, a stability determining section 21 and the vascular center determining section 31.

One of the differences from the first preferred embodiment of the present invention described above is that the apparatus of this preferred embodiment includes the longitudinal axis determining section 20 and the stability determining section 21 and that the reliability determining section 6 uses the results obtained by the longitudinal axis determining section 20 and the stability determining section 21.

Another difference between them is that not only these results of decision but also the results of the vascular center determination and the pulsating status checkout are presented on the display 9.

The probe 1 may be the same as what is used in the first preferred embodiment of the present invention described above. And the ultrasonic signal processing section 2, the tomographic image processing section 3, the vascular center determining section 31, the vascular wall thickness calculating section 4 and the pulsation detecting section 5 perform the same processing as what has already been described for the first preferred embodiment.

That is why the processing steps S201, S202, S203 and S204 of this preferred embodiment may be respectively the same as the processing steps S101, S102, S103 and S104 of the first preferred embodiment described above.

According to this preferred embodiment, the tomographic image information provided by the tomographic image processing section 3 is also output to the longitudinal axis determining section 20. In Step S211, the longitudinal axis determining section 20 determines, based on the luminance information included in the tomographic image information, whether or not the tomographic image information being provided covers a longitudinal cross section of the blood vessel. In this processing step, if it has turned out, based on the luminance distribution of the tomographic image information in the IMT measuring range (see FIG. 18), that the image is being captured in the longitudinal direction of the blood vessel, then tomographic image information can be regarded as covering a longitudinal cross section of the blood vessel. Alternatively, based on the luminance distribution of the tomographic image information in the IMT measuring range and the ratio of a portion of the IMT measuring range in which the image is regarded as being captured in the longitudinal direction of the blood vessel to the entire range, the degree of probability that the tomographic image information covers a longitudinal cross section of the blood vessel may be determined instead of simply determining whether the longitudinal axis is covered or not.

Next, it will be described what processing is carried out by the stability determining section 21. According to this preferred embodiment, the information about the boundaries detected and the vascular wall thickness provided by the vascular wall detecting section 4 is also output to the stability determining section 21. In Step S212, by sensing how the IMT value that has been calculated by the IMT calculating section 42 varies with time in a predetermined period with respect to the boundaries that have been detected by the boundary detecting section 41, the stability determining section 21 calculates the magnitude of variation in the IMT value due to some disturbance such as the motion of the probe 1 or the subject, thereby determining the degrees of stability of the IMT value calculated. In this example, the time for the IMT calculating section 42 to calculate the IMT value is supposed to be the end-diastolic timing.

The IMT value calculated by the IMT calculating section 42 is sent to the stability determining section 21 every cardiac cycle. In response, the stability determining section 21 accumulates the IMT values calculated for a predetermined number of cardiac cycles. Then, the stability determining section 21 may compare the difference between the multiple IMT values accumulated to a predetermined value. And if the difference has turned out to be smaller than the predetermined value, the stability determining section 21 may decide that the IMT value calculated hardly varies in spite of the motion of the probe 1 or the subject and is sufficiently stabilized. Or the stability determining section 21 may also decide that the smaller the difference between the multiple IMT values accumulated, the more stabilized the IMT value calculated should be. In this manner, the stability determining section 21 may determine the degree of stability of the IMT value finely instead of just determining whether the IMT value calculated is a stabilized one or not.

The next two processing steps S205 and S206 of this preferred embodiment may be respectively the same as the processing steps S105 and S106 of the first preferred embodiment described above.

Next, it will be described what processing is carried out by the reliability determining section 6 according to this preferred embodiment. In Step S207, the reliability determining section 6 determines the reliability of the IMT value that has been calculated by the IMT calculating section 42 based on (a) the result of the decision made by the longitudinal axis determining section 20, (b) the result of the decision made by the vascular center determining section 31, (c) the result of the pulsating status checkout made by the pulsating status checking section 52 based on the information provided by the pulsation information processing section 51 and the cardiac cycle detecting section 53, and (d) the result of the decision made by the stability determining section 21. Next, in Step S208, the reliability determining section 6 determines whether or not the IMT value obtained is reliable enough to use as the final result of measurement. If the answer is YES, the control section 7 decides in the next processing step S209 that this IMT value be defined as the result of measurement. Optionally, in this processing step, the processing of freezing the image may be carried out. On the other hand, if the reliability determining section 6 has not found the IMT value obtained reliable enough, then the process goes back to the processing step S201 to carry on the measurement.

Hereinafter, it will be described more exactly how the reliability determining section 6 carries out its reliability determining processing. First of all, (1) if the longitudinal axis determining section 20 has decided that the tomographic image information provided covers a longitudinal cross section of the blood vessel in the IMT measuring range as described above, then the reliability determining section 6 decides that the IMT value obtained be a highly reliable one. Also, (2) if the stability determining section 21 has decided that the magnitude of variation of the IMT value is smaller than a predetermined value and the IMT value is sufficiently stabilized as described above, then the reliability determining section 6 also decides that the IMT value obtained be a highly reliable one. Furthermore, as in the first preferred embodiment described above, (3) if the vascular center determining section 31 has decided that the probe 1 is put in a right position to catch the blood vessel close enough to its center to measure the IMT accurately and (4) if the pulsating status checking section 52 has decided that the pulse of the blood vessel is measured properly, then the reliability determining section 6 also decides that the IMT value obtained be a highly reliable one. And if either all, or at least a predetermined number, of these four conditions (1) through (4) are satisfied, then the reliability determining section 6 decides that the IMT value obtained be reliable enough to use as the final result of measurement.

Alternatively, (5) the longitudinal axis determining section 20 may calculate an estimated value indicating the degree of probability that the tomographic image information provided covers a longitudinal cross section of the blood vessel as described above. (6) The stability determining section 21 may calculate an estimated value indicating the degree of stability of the IMT value calculated as described above. Also, as in the first preferred embodiment described above, (7) the vascular center determining section 31 may calculate an estimated value indicating the probability that the probe 1 is put in a right position to catch the blood vessel close enough to its center. And (8) the pulsating status checking section 52 may calculate an estimated value indicating the probability that the pulse of the blood vessel is measured properly. Based on these four estimated values (5) through (8), the reliability determining section 6 may calculate an estimated value indicating the reliability of the IMT value obtained. And if the estimated value is beyond a predetermined reference value, then the reliability determining section 6 may decide that the IMT value obtained be reliable enough to use as the final result of measurement.

Finally, in Step S210, the image synthesizing section 8 synthesizes together the IMT measured value, which has been regarded as the final result of measurement in accordance with the decision made by the reliability determining section 6, and the tomographic image that has been generated by the tomographic image processing section 3 and then outputs a synthetic image thus obtained to the display 9. Then, the operator can see, with his or her own eyes, whether or not the measurement can be carried out on a cross section of the blood vessel that passes its longitudinal center. As a result, the operator can confirm the result of measurement and its reliability on the screen. Consequently, the present invention contributes to increasing the operability significantly.

Optionally, the result of the decision made by the reliability determining section 6 may also be displayed by itself as characters or a symbol or icon instead of being synthesized with the tomographic image.

Also, those results of the decisions made by the longitudinal axis determining section 20, the vascular center determining section 31, the pulsating status checking section 52 and the stability determining section 21 may be presented on the display 9. By displaying those results of decision, if the reliability of the IMT value obtained has turned out to be low, the user can know exactly why its reliability is low, thus contributing to increasing the operability.

As described above, according to this preferred embodiment, if the longitudinal axis determining section 20 determines whether or not the tomographic image information provided covers a longitudinal cross section of the blood vessel and if the result of the decision is used to determine the reliability, it can be determined more accurately whether or not the received signal has been obtained from a cross section of the blood vessel that passes its longitudinal center. As a result, the IMT value obtained can be a more reliable one.

Also, if the stability determining section 21 determines the degree of stability of the IMT value calculated based on its magnitude of variation and if the result of the decision is used to determine the reliability, then the IMT value that is hardly affected by the motion of the probe 1 or the subject can be defined as the final result of measurement. As a result, the IMT value obtained can be a more reliable one.

In the preferred embodiment described above, the longitudinal axis determining section 20 determines, based on the tomographic image information provided by the tomographic image processing section 3, whether or not the tomographic image information covers a longitudinal cross section of the subject's blood vessel. However, this decision can also be made based on the amplitude of the received echo signal supplied from the ultrasonic signal processing section 2. Then, the decision can be made without depending on the settings or parameters used when the tomographic image is generated.

Furthermore, in the preferred embodiment described above, the vascular center determining section 31 determines, based on the tomographic image information provided by the tomographic image processing section 3, whether or not the received signal has been obtained from a cross section of the blood vessel that passes its longitudinal center. However, this decision can also be made based on the amplitude of the received echo signal supplied from the ultrasonic signal processing section 2. Then, the decision can be made without depending on the settings or parameters used when the tomographic image is generated.

Figure 13:
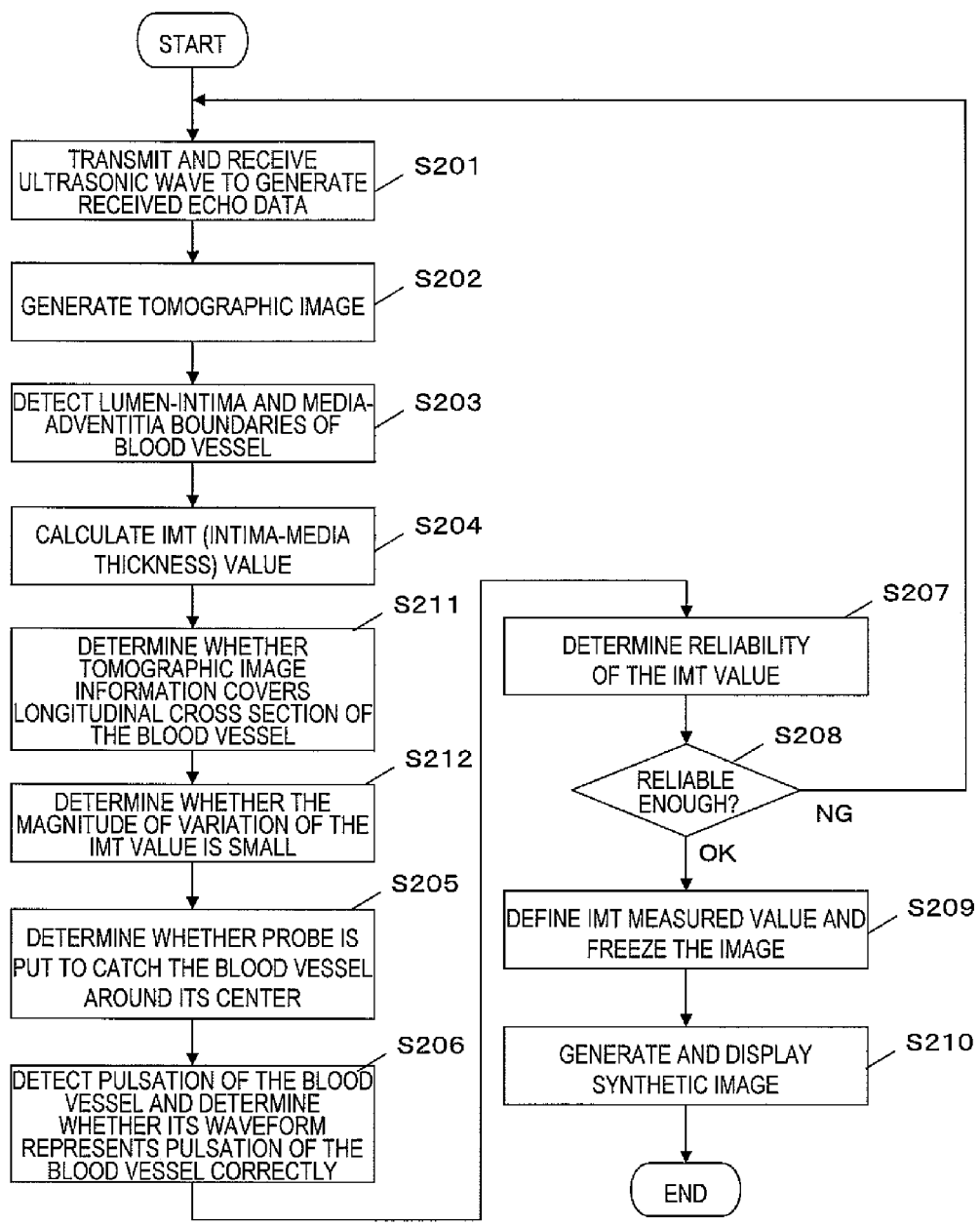
FIG. 13 is a flowchart showing a procedure of operation according to the third preferred embodiment.

In the example illustrated in FIG. 13, the longitudinal axis determining processing step S211, the stability determining processing step S212, the vascular center determining processing step S205 and the pulsating status checkout processing step S206 are supposed to be performed in this order. However, these processing steps may also be performed in any other order.

Furthermore, the apparatus of this preferred embodiment is supposed to include both the longitudinal axis determining section 20 and the stability determining section 21. However, the apparatus may include either only the longitudinal axis determining section 20 or only the stability determining section 21.

Embodiment 4

Figure 14:
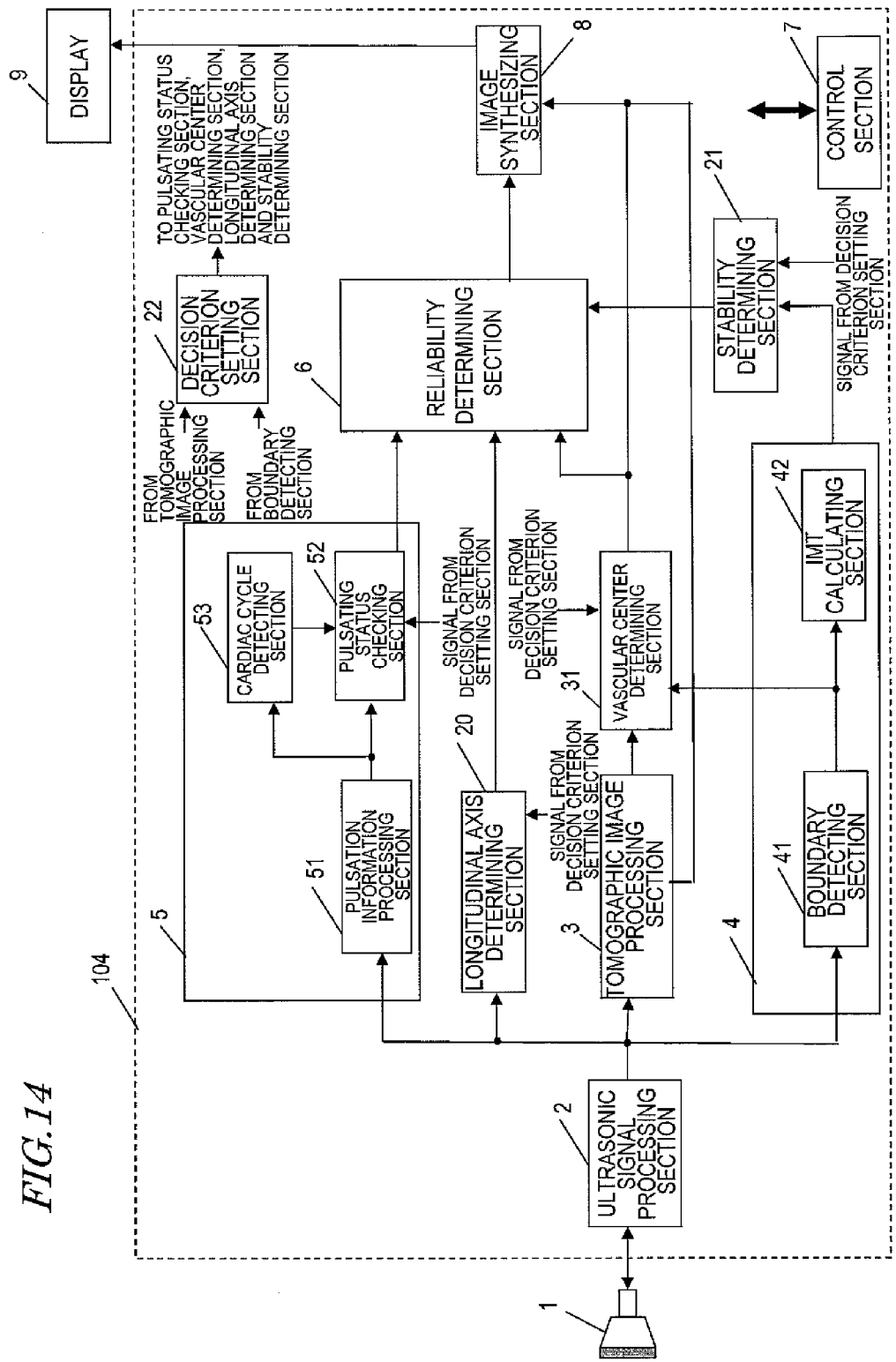
FIG. 14 is a block diagram illustrating a detailed configuration of an ultrasonic diagnostic apparatus as a fourth preferred embodiment of the present invention.

Hereinafter, a fourth specific preferred embodiment of the present invention will be described with reference to FIGS. 14 and 15, which are a block diagram illustrating an ultrasonic diagnostic apparatus as a fourth preferred embodiment of the present invention and a flowchart showing the typical procedure of operation according to the fourth preferred embodiment, respectively.

The ultrasonic diagnostic apparatus 104 of the fourth preferred embodiment of the present invention includes the ultrasonic signal processing section 2, the tomographic image processing section 3, the vascular wall thickness calculating section 4, the pulsation detecting section 5, the reliability determining section 6, the control section 7, the image synthesizing section 8, the longitudinal axis determining section 20, the stability determining section 21, the vascular center determining section 31 and a decision criterion setting section 22.

Unlike the third preferred embodiment of the present invention described above, the apparatus 104 of this preferred embodiment includes a decision criterion setting section 22 that sets criteria of decision for the vascular center determination, the pulsating status checkout, the longitudinal axis determination and the stability determination so as to vary with the feature of the luminance signal in the ROI.

The probe 1 may be the same as what is used in the first preferred embodiment of the present invention described above. The ultrasonic signal processing section 2, the tomographic image processing section 3, the vascular center determining section 31, the vascular wall thickness calculating section 4 and the pulsation detecting section 5 perform the same processing as what has already been described for the first preferred embodiment. And the longitudinal axis determining section 20 and the stability determining section perform the same processing as what has already been described for the third preferred embodiment.

That is why the processing steps S301, S302, S303 and S304 of this preferred embodiment may be respectively the same as the processing steps S101, S102, S103 and S104 of the first preferred embodiment described above.

Next, the decision criterion setting section 22 will be described. In response to a control signal supplied as a trigger from the control section 7 in Step S313, the decision criterion setting section 22 calculates in the next processing step S314 a value representing the feature of a luminance signal around the boundaries based on the tomographic image information provided by the tomographic image processing section 3 and information about the boundaries detected by the boundary detecting section 41. And by changing predetermined values for use to make decisions in the longitudinal axis determining section 20, the stability determining section 21, the vascular center determining section 31 and the pulsating status checking section 52 according to this feature quantity, the decision criterion setting section 22 sets a criterion of decision.

The next four processing steps S311, S312, S305 and S306 of this preferred embodiment may be respectively the same as the processing steps S211 and S212 of the third preferred embodiment described above and the processing steps S105 and S106 of the first preferred embodiment described above.

Then, in Step S307, based on the decisions that have been made by the longitudinal axis determining section 20, the stability determining section 21, the vascular center determining section 31 and the pulsating status checking section 52 using the threshold value that has been set by the decision criterion setting section 22, the reliability determining section 6 determines the reliability of the IMT value obtained.

In a situation where the degree of clearness of the tomographic image rendered has changed with the attribute of the subject's blood vessel or surrounding tissue, if the same criterion of decision were used continuously, then the criterion could be too loose for one subject but could be too strict for another subject. As a result, the accuracy and reliability of the IMT value obtained would decrease. That is why by providing the decision criterion setting section 22 as in this preferred embodiment, the vascular center determination, pulsating status checkout, longitudinal axis determination and stability determination can be carried out according to the attribute of an individual subject's tissue, and therefore, the accuracy and reliability of the IMT value obtained can be increased.

Next, in Step S308, the reliability determining section 6 determines whether or not the IMT value obtained is reliable enough to use as the final result of measurement. If the answer is YES, the control section 7 decides in the next processing step S309 that this IMT value be defined as the result of measurement. Optionally, in this processing step, the processing of freezing the image may be carried out. On the other hand, if the reliability determining section 6 has not found the IMT value obtained reliable enough, then the process goes back to the processing step S301 to carry on the measurement.

The last processing step S310 may be the same as the processing step S210 of the third preferred embodiment described above.

In the preferred embodiment described above, the control signal supplied from the control section 7 is supposed to be used as a trigger. However, the timing when the longitudinal axis determining section 20 decides that the tomographic image provided cover a longitudinal cross section of the blood vessel may also be used as a trigger. In that case, as soon as the tomographic image as viewed in the longitudinal direction has been obtained, the IMT measurement can be started smoothly.

Still alternatively, an input section may be provided and the user's input may also be used as a trigger. In that case, it is possible to have a user who knows very well about how to make an IMT measurement set the criterion of decision.

Figure 15:
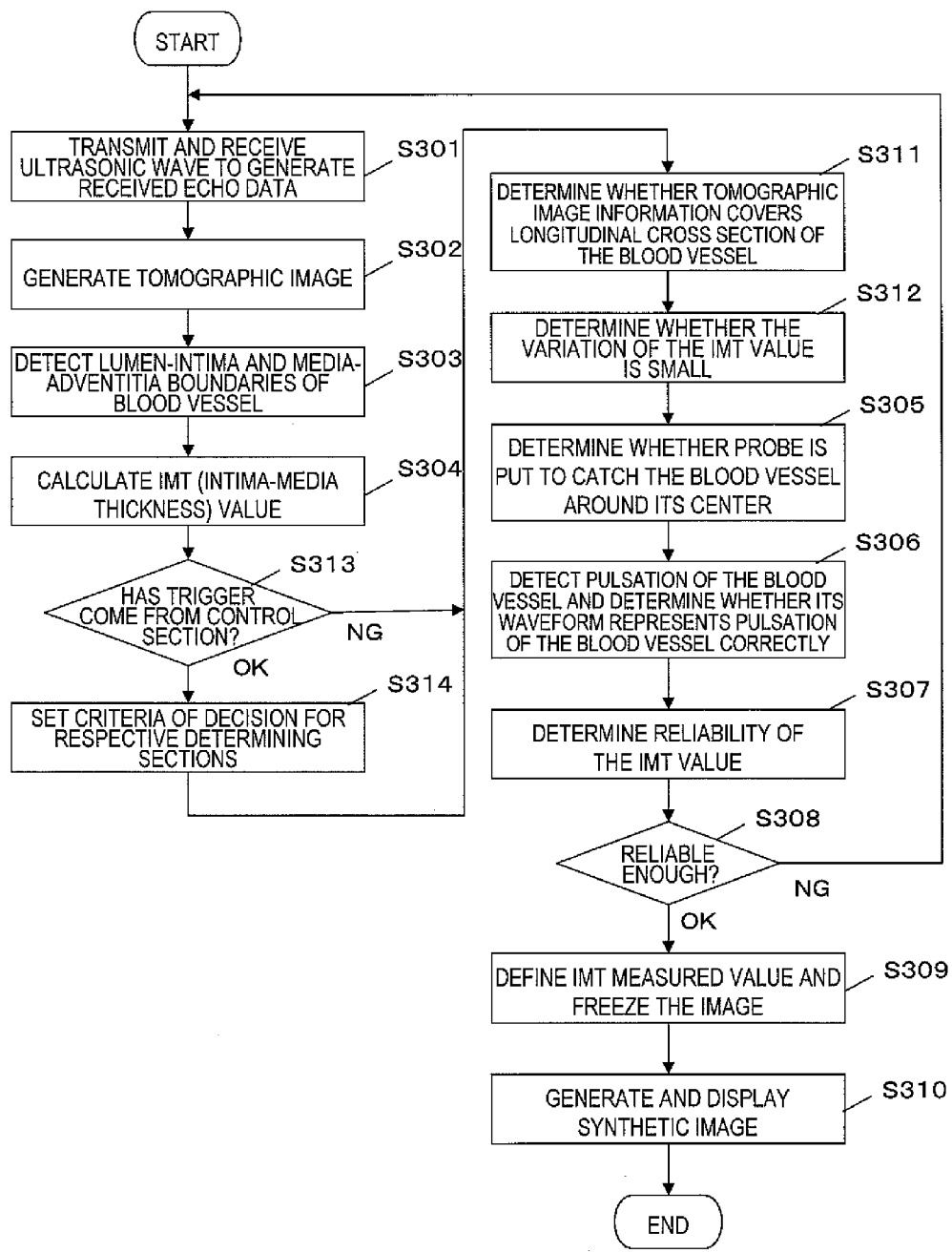
FIG. 15 is a flowchart showing a procedure of operation according to the fourth preferred embodiment.

In the example illustrated in FIG. 15, the longitudinal axis determining processing step S311, the stability determining processing step S312, the vascular center determining processing step S305 and the pulsating status checkout processing step S306 are supposed to be performed in this order. However, these processing steps may also be performed in any other order.

Furthermore, the apparatus of this preferred embodiment is supposed to include both the longitudinal axis determining section 20 and the stability determining section 21. However, the apparatus may include only one of them.

Embodiment 5

Hereinafter, an ultrasonic diagnostic apparatus 105 as a fifth specific preferred embodiment of the present invention will be described with reference to FIG. 15, which is a block diagram illustrating the ultrasonic diagnostic apparatus of the fifth preferred embodiment. In FIG. 15, any functional block also shown in FIG. 2 with the sane reference numeral has substantially the same function as its counterpart of the first preferred embodiment and description thereof will be omitted herein.

In measuring the wall thickness of a blood vessel that is the object of measurement, a reliability determining section 60 determines the degree of reliability of the status monitored or the calculated value (i.e., how reliable the status or value is to use it as a result of measurement) based on the results of measurement or processing obtained by the tomographic image processing section 3, the vascular wall thickness calculating section 4 and the pulsation detecting section 5. Next, a frame storage section 61 stores the degree of reliability that has been determined by the reliability determining section 60, along with the IMT value that has been calculated by the IMT calculating section 42 and the tomographic image that has been generated by the tomographic image processing section 3, as a frame. A best frame choosing section 62 chooses one frame with the highest degree of reliability from all or at least a subset of the frames that are stored in the frame storage section 61.

A control section 70 not only controls the respective functional blocks but also performs a control based on the result of decision made by the reliability determining section 60 so that the result of measurement of the frame that has been chosen by the best frame choosing section 62 is used as the final result of measurement or that the image is frozen on the screen to display the result of measurement of the frame and the tomographic image thereon.

The image synthesizing section 80 is designed so that the display 9 is connectible thereto, and synthesizes the result of measurement of the frame that has been chosen by the best frame choosing section and the tomographic image together so that their synthetic image can be presented on the display 9.

Figure 16:
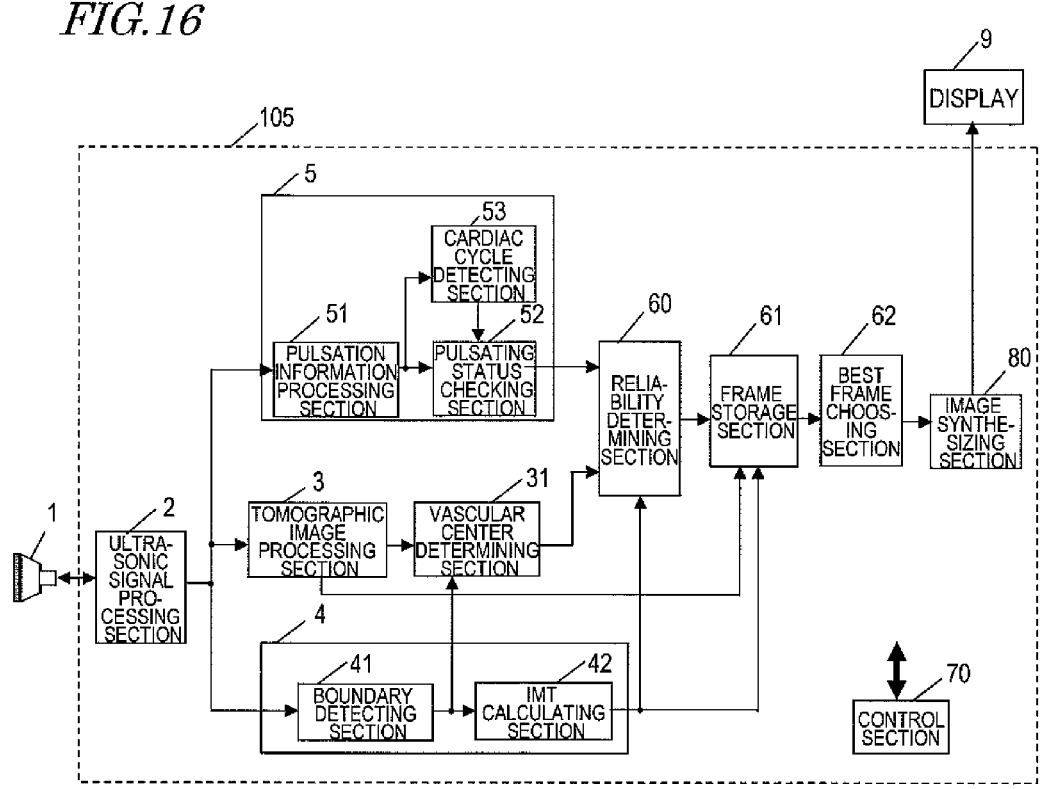
FIG. 16 is a block diagram illustrating a detailed configuration of an ultrasonic diagnostic apparatus as a fifth preferred embodiment of the present invention.
Figure 17:
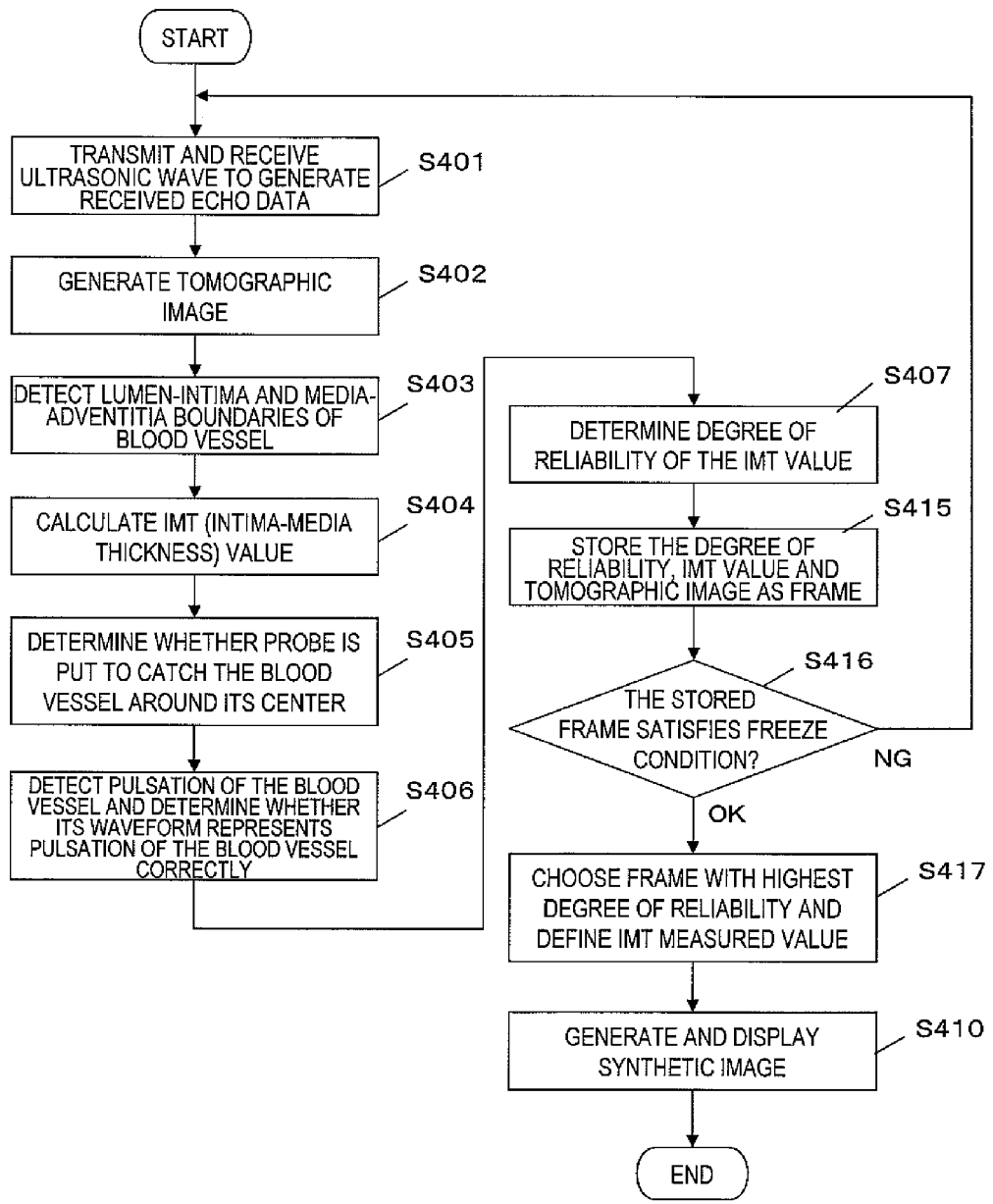
FIG. 17 is a flowchart showing a procedure of operation according to the fifth preferred embodiment.

Hereinafter, it will be described with reference to FIGS. 16 and 17 how the apparatus of this fifth preferred embodiment operates. FIG. 17 is a flowchart showing a typical procedure of operation of the fifth preferred embodiment of the present invention.

First of all, the probe 1, the ultrasonic signal processing section 2, the tomographic image processing section 3, the vascular center determining section 31, the vascular wall thickness calculating section 4 including the boundary detecting section 41 and the IMT calculating section 42, and the best detecting section 5 including the pulsation information processing section 51 and the pulsating status checking section 52 operate in the same way as their counterparts of the first preferred embodiment described above. Thus, the processing steps S401, S402, S403, S404, S405 and S406 are respectively the same as the processing steps S101, S102, S103, S104, S105 and S106 of the first preferred embodiment described above.

Next, in Step S407, the reliability determining section 60 examines the pulsating status that has been detected and checked by the vascular center determining section 31 and the pulsating status checking section 52, thereby determining the degree of reliability of the IMT value that has been calculated by the IMT calculating section 42. And the reliability determining section 60 determines the degree of reliability indicating how reliable the IMT value obtained is to use it as the result of measurement. In this processing step, the vascular center determining section 31 calculates an estimated value indicating the degree of probability that the probe 1 is put in a right position to catch the blood vessel around its center, while the pulsating status checking section 52 calculates an estimated value indicating the degree of probability that the pulse of the blood vessel is being measured properly. And the reliability determining section 60 decides that the greater these estimated values, the higher the degree of reliability the IMT value obtained have. The vascular center determining section 31 and the pulsating status checking section 52 calculate the estimated values in the same way as what has already been described for the first preferred embodiment, and description thereof will be omitted herein. Then, in Step S415, the degree of reliability determined, as well as the IMT value that has been calculated by the IMT calculating section 42 and the tomographic image that has been generated by the tomographic image processing section 3, is stored as a frame in the frame storage section 61.

The processing step S416 will be described later.

Finally, in Step S417, in accordance with the instruction given by the control section 7, the best frame choosing section 62 retrieves the frames that are stored in the frame storage section 61 and chooses a frame with the highest degree of reliability from all or a subset of the frames. And the control section 7 decides that the IMT value of the chosen frame be defined as the IMT measured value. The timing when the control section 7 gives that instruction may be when the image is frozen by the control section 7 in accordance with the user's command or the decision made by the reliability determining section 60 as will be described later.

In this case, the apparatus may be designed, as in Step S416, so that the reliability determining section 60 performs the processing of getting the image frozen by the control section 7 only when some conditions are satisfied. Specifically, the image may be frozen when at least a certain number of frames, of which the degrees of reliability are higher than a predetermined value, are written in the frame storage section 61 or when the number of such frames, of which the degrees of reliability are higher than a predetermined value and which have been written consecutively in the frame storage section 61, reaches a certain number. Particularly in the latter case, if multiple frames with high degrees of reliability have been written consecutively, then it can be said that the measurement has been done appropriately with good stability. That is why the best frame choosing section preferably chooses a frame with the highest degree of reliability from those consecutive frames. If the condition for freezing is not satisfied, however, the process goes back to the processing step 401 to carry on the measurement.

In the example illustrated in FIG. 17, the vascular center determining processing step S405 and the pulsating status checkout processing step S406 are supposed to be performed in this order. However, these processing steps may be carried out in reverse order, too.

By getting these processing steps done by the apparatus with such a configuration, the IMT measured value and a tomographic image representing the blood vessel can be reliable enough to use as the final result of measurement.

In this case, the reliability determining section 60 can make the decision based on either only the result obtained by the vascular center determining section 31 or just the one obtained by the pulsating status checking section 52. If both of these two results are relied on, the accuracy of the decision can be increased. Nevertheless, depending on the situation of the inspection, the decision can also be made based on only of those two results. That is why the given software programs may be selectively used appropriately according to the application, cost and weight of the apparatus as in the first preferred embodiment described above.

Optionally, the ultrasonic diagnostic apparatus 105 may also be modified so as to further include the longitudinal axis determining section 20 and stability determining section 21 that have already been described for the third preferred embodiment of the present invention. In that case, the reliability determining section 60 will determine the degree of reliability of the IMT value that has been calculated by the IMT calculating section 42 based on not only the results obtained by the vascular center determining section 31 and the pulsating status checking section 52 but also the ones obtained by the longitudinal axis determining section 20 and the stability determining section 21 as well. In such a modified example, besides the estimated value indicating the degree of probability that the probe 1 is put in a right position to catch the blood vessel around its center and the estimated value indicating the degree of probability that the pulse of the blood vessel is being measured properly, another estimated value is calculated by the longitudinal axis determining section 20 to indicate the degree of probability that the tomographic image information provided covers a longitudinal cross section of the blood vessel. On the other hand, still another estimated value is calculated by the stability determining section 21 to indicate the degree of stability of the IMT value calculated. And the reliability determining section 60 decides that the greater these four estimated values, the higher the degree of reliability of the IMT value obtained. The longitudinal axis determining section 20 and the stability determining section 21 calculate the estimated values just as already described for the third preferred embodiment, and description thereof will be omitted herein. Consequently, the performance of the reliability decision can be further increased.

Optionally, the ultrasonic diagnostic apparatus 105 may also be modified so as to further include the decision criterion setting section 2 that has already been described for the fourth preferred embodiment of the present invention. In that case, the apparatus may be designed to set the criterion of decision by changing the predetermined values for use to make decisions in the longitudinal axis determining section 20, the stability determining section 21, the vascular center determining section 31 and the pulsating status checking section 52 in response to the control signal supplied from the control section 7 as a trigger. In such a modified example, the decision criterion setting section 22 will operate in the same way, and will achieve the same effects, as in the fourth preferred embodiment described above, and description thereof will be omitted herein.

Finally, in Step S410, the image synthesizing section 80 synthesizes together the IMT measured value of the frame that has been chosen by the best frame choosing section in accordance with the decision made by the reliability determining section 60 and the tomographic image, and then outputs the synthetic image thus obtained to the display 9. As a result, the operator can monitor the diagnostic image and the result of measurement on the screen.

Although not shown, the pulsation detecting section of this ultrasonic diagnostic apparatus may also be replaced with the pulsation detecting section 50 of the second preferred embodiment that uses the ECG pads 12. The difference between this preferred embodiment shown in FIG. 16 and that alternative preferred embodiment and their respective features are the same as the relation between the first and second preferred embodiments of the present invention, and a detailed description thereof will be omitted herein.

Consequently, the present invention provides an ultrasonic diagnostic apparatus that can achieve not only the effect of getting the IMT value measured more easily with increased operability but also the effect of measuring the IMT more accurately as well while making an inspection.

INDUSTRIAL APPLICABILITY

According to the ultrasonic diagnostic apparatus and intima-media thickness (IMT) measuring method of the present invention, it is determined whether the blood vessel that is the object of IMT measurement is inspected in an appropriate state (e.g., whether the probe is put in a right position) and at the best timing. And the IMT value that has been obtained at such timing is used as the final result of measurement. As a result, the IMT measured value can be a highly reliable one, thus contributing to significantly increasing the accuracy and operability of the inspection of arterial sclerosis, for example. Consequently, the present invention is effectively applicable to an ultrasonic diagnostic apparatus and a method for measuring an IMT using such an apparatus.

REFERENCE SIGNS LIST 1 probe
2 ultrasonic signal processing section
3 tomographic image processing section
4 vascular wall thickness calculating section
5 pulsation detecting section
6 reliability determining section
7 control section
8 image synthesizing section
9 display
10 blood vessel
11 subject's skin surface
12 ECG pad
20 longitudinal axis determining section
21 stability determining section
22 decision criterion setting section
31 vascular center determining section
41 boundary detecting section
42 IMT calculating section
50 pulsation detecting section
51 pulsation information processing section
52 pulsating status checking section
53 cardiac cycle detecting section
54 ECG signal processing section
55 cardiac cycle detecting section
60 reliability determining section
61 frame storage section
62 best frame choosing section
70 control section
80 image synthesizing section
101, 102, 103, 104, 105 ultrasonic diagnostic apparatus

The invention claimed is:

1. An ultrasonic diagnostic apparatus, to which a probe with a transducer is connectible, the apparatus comprising:
an ultrasonic signal processing section, which performs transmission processing for transmitting an ultrasonic wave toward a subject's blood vessel by driving the probe and performs reception processing for generating a received signal based on the ultrasonic wave that has been reflected from the subject's blood vessel and received at the probe;
a tomographic image processing section, which generates a tomographic image based on the received signal;
a boundary detecting section, which detects the lumen-intima and media-adventitia boundaries of the blood vessel based on either the received signal or the tomographic image;
a vascular wall thickness calculating section, which calculates, as a vascular wall thickness value, the interval between the lumen-intima and media-adventitia boundaries that have been detected by the boundary detecting section;
a vascular center determining section, which determines the probe is located over around a longitudinal center of the blood vessel when it has been detected that a length of a portion of the tomographic image in which a signal intensity or luminance distribution is unique to the lumen-intima and media-adventitia boundaries is longer than a predetermined length;
a reliability determining section, which determines reliability of the vascular wall thickness value based on either a signal feature of the received signal or an image information feature of the tomographic image at a location on any of the lumen-intima and media-adventitia boundaries that have been detected and based on a determined result of the vascular center determining section; and
a control section, which decides, in accordance with the decision made by the reliability determining section, that the vascular wall thickness value be defined as an intima-media thickness.

2. The ultrasonic diagnostic apparatus of claim 1, wherein the signal feature includes at least one of a signal intensity and a signal intensity distribution.

3. The ultrasonic diagnostic apparatus of claim 1, wherein the image information feature includes at least one of a luminance, a luminance distribution and a shape.

4. The ultrasonic diagnostic apparatus of claim 1, wherein the vascular center determining section further calculates an estimated value indicating the probability that the received signal has been obtained from around the cross section of the blood vessel that passes its longitudinal center,
wherein if the vascular center determining section has decided that the probe is located over around the cross section of the blood vessel that passes its longitudinal center or if the estimated value is beyond a predetermined reference value, the reliability determining section decides that the vascular wall thickness value have a high reliability or the reliability determining section decides that the higher the estimated value is, the higher the reliability of the vascular wall thickness value.

5. The ultrasonic diagnostic apparatus of claim 4, further comprising a decision criterion setting section that sets, by reference to the received signal obtained from the subject's blood vessel or information about the tomographic image generated by the tomographic image processing section and the boundary detected by the boundary detecting section, a criterion of decision for use to perform the vascular center determining process, a pulsating status checkout process, a longitudinal axis determining process or a stability determining process.

6. The ultrasonic diagnostic apparatus of claim 1, further comprising a pulsation detecting section, which checks the pulsating status of the blood vessel, thereby either determining whether the pulse of the blood vessel is being measured properly or calculating an estimated value indicating the probability that the pulse of the blood vessel is being measured properly,
wherein the pulsation detecting section checks the pulsating status of the blood vessel by sensing a variation in the inside diameter of the blood vessel, and decides that the pulse of the blood vessel is being measured properly if the variation in the inside diameter of the blood vessel agrees with a reference pulse wave form.

7. The ultrasonic diagnostic apparatus of claim 6, wherein the pulsation detecting section checks the pulsating status by detecting a feature quantity of the variation in the inside diameter of the blood vessel.

8. The ultrasonic diagnostic apparatus of claim 6, wherein the pulsation detecting section checks the pulsating status based on the correlation between a waveform representing the variation in the inside diameter of the blood vessel and a preregistered model waveform.

9. The ultrasonic diagnostic apparatus of claim 6, wherein the pulsation detecting section includes a cardiac cycle detecting section that detects a particular timing during one cardiac cycle and that either determines whether or not the pulse of the blood vessel is being measured properly before and/or after the detected timing or calculates an estimated value indicating the probability that the pulse of the blood vessel is being measured properly before and/or after the detected timing,
 wherein if the pulsation detecting section has decided that the pulse of the blood vessel be being measured properly before and/or after the detected timing or if the estimated value is beyond a predetermined reference value, the reliability determining section decides that the vascular wall thickness value have a high reliability or the reliability determining section decides that the higher the estimated value, the higher the reliability of the vascular wall thickness value.

10. The ultrasonic diagnostic apparatus of claim 9, wherein the pulsation detecting section checks the pulsating status by sensing a motion of the subject's tissue based on the received signal, and wherein the cardiac cycle detecting section detects the particular timing during the cardiac cycle based on the pulsating status.

11. The ultrasonic diagnostic apparatus of claim 9, wherein the cardiac cycle detecting section detects the timing based on an electrocardiographic complex.

12. The ultrasonic diagnostic apparatus of claim 9, wherein the timing detected by the cardiac cycle detecting section is an end-diastolic timing.

13. The ultrasonic diagnostic apparatus of claim 9, wherein the timing detected by the cardiac cycle detecting section is later than an end-diastolic timing by a predetermined amount of time.

14. The ultrasonic diagnostic apparatus of claim 1, further comprising a longitudinal axis determining section that either determines whether or not the received signal or the tomographic image covers a longitudinal cross section of the subject's blood vessel or calculates an estimated value indicating the probability that the received signal or the tomographic image covers a longitudinal cross section of the subject's blood vessel,
 wherein if the longitudinal axis determining section has decided that the received signal or the tomographic image covers a longitudinal cross section of the subject's blood vessel or if the estimated value is beyond a predetermined reference value, the reliability determining section decides that the vascular wall thickness value have a high reliability or the reliability determining section decides that the higher the estimated value, the higher the reliability of the vascular wall thickness value.

15. The ultrasonic diagnostic apparatus of claim 1, further comprising a stability determining section that either determines, by the magnitude of invariability of the vascular wall thickness value with time, whether or not the vascular wall thickness value is a stabilized one or calculates, based on the magnitude of invariability of the vascular wall thickness value with time, the probability that the vascular wall thickness value is a stabilized one,
 wherein if the stability determining section has decided that the vascular wall thickness value is a stabilized one or if the estimated value is beyond a predetermined reference value, the reliability determining section decides that the vascular wall thickness value have a high reliability or the reliability determining section decides that the higher the estimated value, the higher the reliability of the vascular wall thickness value.

16. The ultrasonic diagnostic apparatus of claim 1, further comprising an image synthesizing section that synthesizes together the decision made by the reliability determining section and the tomographic image generated by the tomographic image processing section,
 wherein a synthetic image obtained by the image synthesizing section is displayed.

17. The ultrasonic diagnostic apparatus of claim 1, wherein the ultrasonic signal processing section performs the transmission processing and the reception processing a number of times, thereby sequentially generating multiple received signals, and
 wherein the tomographic image processing section sequentially generates multiple tomographic images based on the multiple received signals, and
 wherein the boundary detecting section sequentially detects the lumen-intima and media-adventitia boundaries of the blood vessel based on each of the multiple received signals or each of the multiple tomographic images, and
 wherein the vascular wall thickness calculating section sequentially calculates the vascular wall thickness values based on the lumen-intima and media-adventitia boundaries of the blood vessel that have been detected sequentially, and
 wherein the reliability determining section sequentially determines the degrees of reliability of the vascular wall thickness values that have been calculated sequentially, and
 wherein the control section decides, in accordance with the decision made by the reliability determining section, that the vascular wall thickness value be defined as an intima-media thickness, and
 wherein at least the tomographic images generated sequentially are displayed.

18. The ultrasonic diagnostic apparatus of claim 17, wherein in accordance with the decision made by the reliability determining section, the control section freezes the tomographic images that are displayed sequentially.

19. The ultrasonic diagnostic apparatus of claim 17, further comprising a frame storage section, which sequentially stores, as frames, the tomographic images, the vascular wall thickness values and the decision made by the reliability determining section, and
 a best frame choosing section, which chooses a frame with the highest reliability from either all or a subset of the frames that have been stored in the frame storage section,
 wherein the control section decides that the vascular wall thickness value calculated by the vascular wall thickness calculating section on the frame that has been chosen by the best frame choosing section be defined as the intima-media thickness.

20. The ultrasonic diagnostic apparatus of claim 19, wherein if at least a certain number of frames, of which the vascular wall thickness values have degrees of reliability that are higher than a predetermined value, have been written in the frame storage section, the control section freezes the tomographic images that are displayed sequentially.

21. The ultrasonic diagnostic apparatus of claim 19, wherein when the number of frames, of which the vascular wall thickness values have degrees of reliability that are higher than a predetermined value and which have been written consecutively in the frame storage section, reaches a particular number, the control section freezes the tomographic images that are displayed sequentially.

22. The ultrasonic diagnostic apparatus of claim 21, wherein the best frame choosing section chooses a frame with the highest reliability from the particular number of frames, of which the degrees of reliability are higher than the predetermined value and which have been written consecutively in the frame storage section.

23. The ultrasonic diagnostic apparatus of claim 1, wherein the predetermined length is a predefined percentage of an IMT measuring range.

24. A method for measuring an intima-media thickness, the method comprising the steps of:
  performing reception processing for generating a received signal based on an ultrasonic wave that has been reflected from a subject's blood vessel and received at a probe;
  generating a tomographic image based on the received signal;
  detecting the lumen-intima and media-adventitia boundaries of the blood vessel based on either the received signal or the tomographic image;
  calculating, as a vascular wall thickness value, the interval between the lumen-intima and media-adventitia boundaries that have been detected;
  performing a center determining process that determines the probe is over around a longitudinal center of the blood vessel when it has been detected that a length of a portion of the tomographic image in which a signal intensity or luminance distribution is unique to the lumen-intima and media-adventitia boundaries is longer than a predetermined length;
  determining the reliability of the vascular wall thickness value based on either a signal feature of the received signal or an image information feature of the tomographic image at a location on any of the lumen-intima and media-adventitia boundaries that have been detected and based on a result of the center determining process; and
  deciding, in accordance with the decision made, that the vascular wall thickness value calculated be defined as the intima-media thickness.

25. The method of claim 24, further comprising the steps of:
  performing pulsating determining process that determines the pulse of the blood vessel is being measured properly if the variation in the inside diameter of the blood vessel agrees with a reference pulse wave form;
  determining the reliability of the vascular wall thickness value based on either a signal feature of the received signal or an image information feature of the tomographic image at a location on any of the lumen-intima and media-adventitia boundaries that have been detected, and based on a result of the center determining process and a result of the pulsating determining process; and
  deciding, in accordance with the decision made, that the vascular wall thickness value calculated be defined as the intima-media thickness.

26. The method of claim 24, wherein the predetermined length is a predefined percentage of an IMT measuring range.

* * * * *